United States Patent [19]

Miyazaki et al.

[11] 4,427,581

[45] Jan. 24, 1984

[54] PEPTIDE, PROCESS FOR PREPARATION THEREOF AND USE THEREOF

[75] Inventors: Yoshio Miyazaki, Itami; Osamu Nakaguchi, Toyonaka; Masashi Hashimoto, Takarazuka, all of Japan

[73] Assignee: Fujisawa Pharmaceutical Co., Ltd., Osaka, Japan

[21] Appl. No.: 341,058

[22] Filed: Jan. 20, 1982

[30] Foreign Application Priority Data

Jan. 29, 1981 [GB] United Kingdom ................ 8102705
Jun. 29, 1981 [GB] United Kingdom ................ 8120033
Jul. 24, 1981 [GB] United Kingdom ................ 8122991

[51] Int. Cl.$^3$ .......................................... C07C 103/52
[52] U.S. Cl. .......................................... 260/112.5 R
[58] Field of Search ................ 424/177; 260/112.5 R

[56] References Cited

U.S. PATENT DOCUMENTS 4,207,234  6/1980  Kamiya et al. ................ 260/239 A

FOREIGN PATENT DOCUMENTS 11283    5/1980  European Pat. Off. .
2529941  4/1976  Fed. Rep. of Germany .
1519495  7/1978  United Kingdom .
2033906  5/1980  United Kingdom .
2053231  2/1981  United Kingdom .

OTHER PUBLICATIONS

Hosoda et al., Chem. Abs., 87, 100673m, (1977).
Biochemistry, vol. 9, No. 4, 1970, pp. 823-831, (Dezelee et al).
Biochemical and Biophysical Research Communications, vol. 59, No. 4, 1979, pp. 1317-1325, (Ellouz et al).
Agricultural and Biological Chemistry, 41(5), 1977, pp. 763-768, (Nakamura et al).
Abstracts of the Eleventh International Congress on Chemotherapy, Oct. 1-5, 1979, Abstract-702, (Werner et al).
11th International Congress of Chemotherapy, 19th Interscience Conference on Antimicrobial Agents and Chemotherapy-Oct. 1979, Werner et al.-Immunopotentiating Activities of Microbial Tetrapeptides after Coupling with Lauric Acid.
Chemical Abstracts, vol. 88, No. 9, (1978), p. 284, No. 61100w, (Hosoda et al).

*Primary Examiner*—Delbert R. Phillips
*Assistant Examiner*—F. T. Moezie
*Attorney, Agent, or Firm*—Oblon, Fisher, Spivak, McClelland & Maier

[57] ABSTRACT

The invention deals with novel peptides useful in the therapeutic treatment of infectious diseases caused by pathogenic microorganisms, having the structure:

$$R^1-(HNCHOC)_n-HNCH-R^3$$
with $R^2$ on the second carbon, $(CH_2)_2$ chain to $CO-A-NH-$ group bonded to a $\beta$-lactam ring bearing $R^5$ and $N-R^6$ wherein
R$^1$ is hydrogen or acyl;
R$^2$ is lower alkyl;
R$^3$ is carboxy or protected carboxy;
A is a bond, a group of the formula:

$$-HN-CH(CH_2)_k-O-\langle\text{phenyl}\rangle-X-CO-$$
with COOH on the CH wherein X is a group of the formula:

$$-\overset{NOH}{\underset{\|}{C}}-,\ -\overset{O}{\underset{\|}{C}}-\ \text{or}\ -\overset{NHX^1}{\underset{|}{CH}}-$$

wherein X$^1$ is hydrogen or an amino protective group, and
k is an integer of 1 to 4; or a group of the formula:

$$-HNCHCO-\langle\text{phenyl-O}\rangle_l$$
with $R^4\text{-}C_m\text{-}H_{2m-1}\text{-}R^7$ substituent wherein R$^4$ is amino or protected amino,
R$^7$ is carboxy, or protected carboxy,
m is an integer of 1 to 8, and l is an integer of 1 or 0;
R$^5$ is hydrogen, carboxy or esterified carboxy;
R$^6$ is hydrogen, ar(lower)alkyl wherein the alkyl moiety may have carboxy or protected carboxy and the aryl moiety may have one or more substituents selected from hydroxy, protected hydroxy and lower alkoxy; and
n is an integer of 1 or 0.

61 Claims, No Drawings

PEPTIDE, PROCESS FOR PREPARATION THEREOF AND USE THEREOF

This invention relates to a new peptide. More particularly, this invention relates to a new peptide and the pharmaceutically acceptable salt thereof, which have pharmacological activities, to processes for the preparation thereof and to a new intermediate for preparing the active peptide, and to the pharmaceutical composition comprising the same and a method of use thereof.

A new peptide of this invention is represented by the following formula (I):

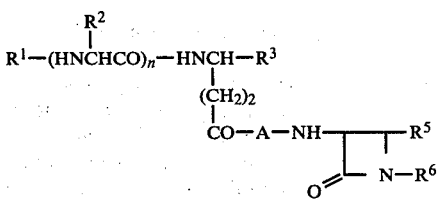

wherein
$R^1$ is hydrogen or acyl;
$R^2$ is lower alkyl;
$R^3$ is carboxy or protected carboxy;
A is a bond, a group of the formula:

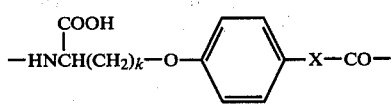

wherein X is a group of the formula:

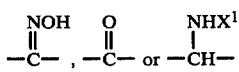

wherein $X^1$ is hydrogen or an amino protective group, and k is an integer of 1 to 4, or a group of the formula:

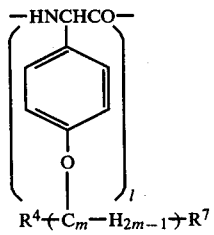

wherein $R^4$ is amino or protected amino,
$R^7$ is carboxy or protected carboxy, m is an integer of 1 to 8, and l is an integer of 1 or 0;
$R^5$ is hydrogen, carboxy or esterified carboxy;
$R^6$ is hydrogen, ar(lower)alkyl wherein the alkyl moiety may have carboxy or protected carboxy and the aryl moiety may have one or more substituents selected from hydroxy, protected hydroxy and lower alkoxy; and
n is an integer of 1 or 0.

Particulars of the various definitions, which are mentioned herinabove and hereinafter, and preferred examples thereof are explained in the following.

The term "lower" is intended to mean a group having 1 to 8 carbon atoms, unless otherwise provided.

(1) Re. Acyl for $R^1$ and $R_a^1$:
As suitable examples of acyl, there may be exemplified alkanoyl, alkoxycarbonyl, aralkanoyl, aralkoxycarbonyl or the like.

As suitable example of alkanoyl, there may be exemplified acetyl, propionyl, butyryl, isobutyryl, valeryl, isovaleryl, pivaloyl, hexanoyl, α-ethylhexanoyl, heptanoyl, octanoyl, lauroyl, stearoyl, n-docosanoyl and the like.

As suitable examples of alkoxycarbonyl, there may be exemplified lower alkoxycarbonyl such as, methoxycarbonyl, ethoxycarbonyl, propoxycarbonyl, butoxycarbonyl, t-butoxycarbonyl or the like.

In the above exemplified alkanoyls or alkoxycarbonyl, the aliphatic hydrocarbon moiety may have optionally one or more suitable substituent(s) such as amino, halogen (e.g. fluorine, chlorine, bromine, etc.), hydroxy, carboxy and the like.

Among said substituted alkanoyls, as suitable examples there may be exemplified hydroxy(lower)alkanoyl such as 2-hydroxypropionyl (i.e. lactoyl).

As suitable examples of aralkoxycarbonyl, there may be exemplified phenyl(lower)alkoxycarbonyl such as benzyloxycarbonyl or the like.

As suitable example of aralkanoyl, there may be exemplified ar(lower)alkanoyl such as phenyl(lower)alkanoyl (e.g. phenylacetyl, etc.) or the like.

In the above exemplified aralkanoyl or aralkoxycarbonyl, the aromatic hydrocarbon moiety and/or the aliphatic hydrocarbon moiety have have optionally one or more suitable substituent(s) such as the same as those exemplified as the suitable substituent for the alkanoyl.

Among said substituted aralkanoyl, as suitable examples there may be exemplified phenyl(lower)hydroxyalkanoyl such as mandelyl and the like.

In the above exemplified acyl, in case that said acyl has one or more functional group(s) such as hydroxy, amino and carboxy, such a functional group may be protected by a conventional protective group to form protected hydroxy, protected amino and protected carboxy.

(2) Re. Lower alkyl for $R^2$:
Suitable example of lower alkyl is one having 1 to 6 carbon atoms such as methyl, ethyl, propyl, isopropyl, butyl, isobutyl, pentyl, isopentyl and the like.

(3) Re. Protected carboxy for $R^3$, $R_a^3$, $R^7$, $R_a^7$ and $R^6$, $R_a^6$ and functional group in the acyl for $R^1$ and $R_a^1$:
A protective group of the protected carboxy includes a conventional carboxy protective group which is conventionally used in the field of amino acid and peptide chemistry.

As suitable examples of protected carboxy, there may be exemplified an ester such as an ester with silyl compound, an ester with an aliphatic hydroxy compound and an ester with a hydroxy compound containing an aromatic group, and a protected carbazolyl of the formula:—CONHNHY (wherein Y is hydrogen or an amino protective group).

As more suitable examples of protected carboxy, there may be exemplified alkyl such as lower alkyl (e.g. methyl, ethyl, etc.) ester, aralkyl such as mono- or diphenyl(lower)alkyl (e.g. benzyl, diphenylmethyl, etc.) ester and the like.

(4) Re. Esterified carboxy for $R^5$:
Esterified carboxy includes a conventional one and there may be exemplified, as suitable examples, the same esters as illustrated above for explanation of protected carboxy.

(5) Re. Amino protective group of protected amino for $R^4$, $R_a^4$, amino protective group for $R_b^4$, $X^1$ and Y, and the function group in the acyl group for $R^1$ and $R_a^1$:

The amino protective group includes a conventional amino protective group which is used in the field of amino acid and peptide chemistry.

As suitable examples of the amino protective group, there may be exemplified alkoxycarbonyl such as lower alkoxycarbonyl (e.g. methoxycarbonyl, ethoxycarbonyl, propoxycarbonyl, butoxycarbonyl, t-butoxycarbonyl, t-pentoxycarbonyl, etc.), aralkoxycarbonyl such as phenyl(lower)alkoxycarbonyl (e.g. benzyloxycarbonyl, etc.) and the like.

(6) Re. Hydroxy protective moiety of protected hydroxy moiety for $R^6$ and $R_c^6$ and hydroxy protective group in the acyl for $R^1$ and $R_a^1$:

As suitable example of a hydroxy protective group in the acyl group for $R^1$ and $R_a^1$, there may be exemplified a conventional one, for example, acyl such as alkanoyl (e.g. acetyl, etc.).

(7) Re. Lower alkoxy for $R^6$, $R_b^6$ and $R_c^6$:

As suitable examples of lower alkoxy, there may be exemplified ($C^1$ to $C^5$) alkoxy such as methoxy, ethoxy, propoxy, butoxy or the like.

(8) Re. Ar(lower)alkyl wherein the alkyl moiety may have carboxy or protected carboxy, and the aryl moiety may have one or more substituents selected from hydroxy, protected hydroxy and lower alkoxy for $R^6$:

As suitable example of ar(lower)alkyl, there may be exemplified phenyl($C^1$ to $C^5$)alkyl such as benzyl, phenetyl, phenylpropyl or the like.

The alkyl moiety of said ar(lower)alkyl may have carboxy or protected carboxy, and the aryl moiety have one or more substituents selected from hydroxy, protected hydroxy and lower alkoxy (e.g. methoxy, ethoxy, propoxy, etc.).

Suitable examples of ar(lower)alkyl having said substituents are a group of the following formula:

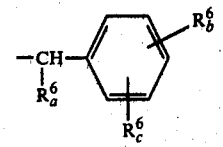

wherein
$R_a^6$ is hydrogen, carboxy or protected carboxy,
$R_b^6$ is hydrogen or lower alkoxy, and
$R_c^6$ is hydroxy, protected hydroxy or lower alkoxy.

A pharmaceutically acceptable salt of the new peptides of the formula (I) may include a salt with an inorganic or organic base such as an alkali metal salt (e.g. sodium salt, potassium salt, etc.), an alkaline earth metal salt (e.g. calcium salt, etc.), ammonium salt, organic amine salt (e.g. ethanolamine salt, triethylamine salt, dicyclohexylamine salt, etc.) or the like, and an acid addition salt with organic or inorganic acid such as methane sulfonate, hydrochloride, sulfate, nitrate, phosphate or the like.

The compound (I) of this invention can be prepared by various methods, details of which will be apparent from the following descriptions.

(1) Process 1: Peptide bond formation:

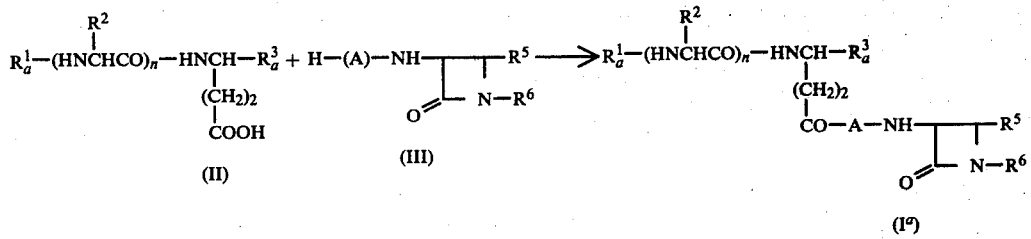

(2) Process 2: Selection deacylation:

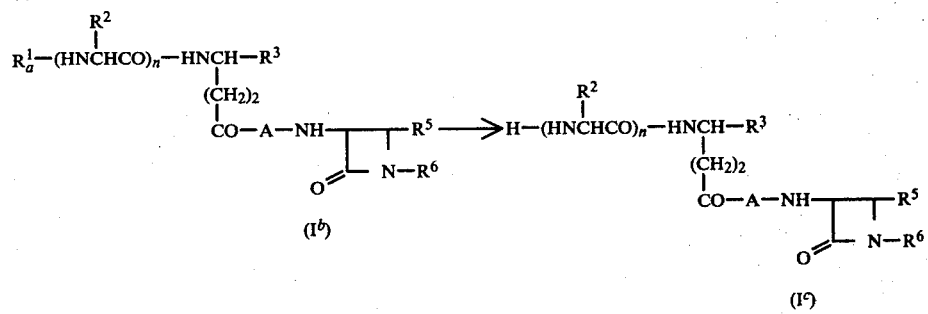

(3) Process 3: Acrylation:

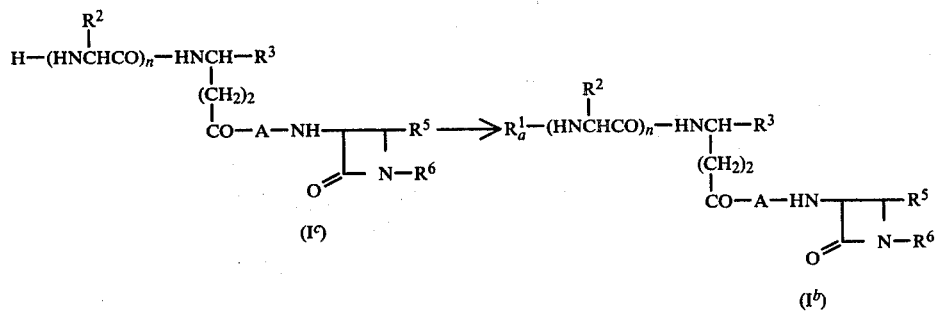
(Iᶜ) → (Iᵇ)

(4) Process 4: Elimination of protective group:

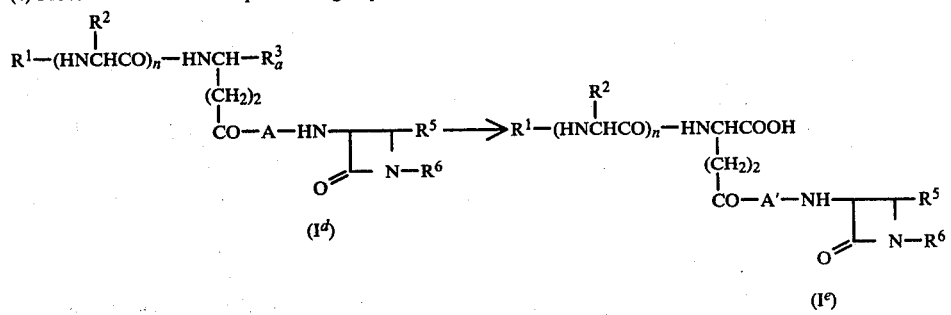
(Iᵈ) → (Iᵉ)

(5) Process 5: Reduction

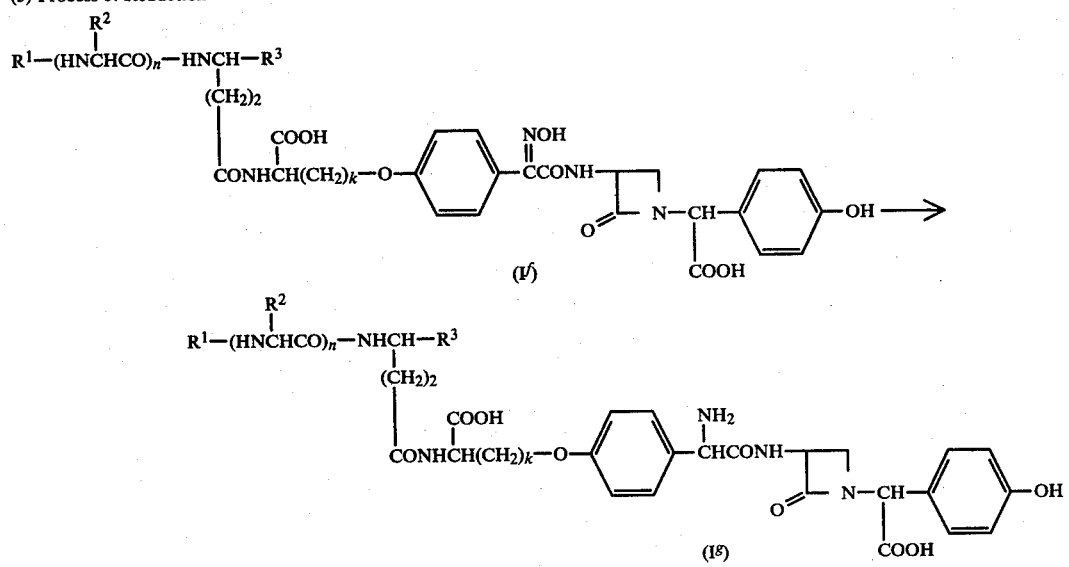
(Iᶠ) → (Iᵍ)

In the above formulae, $R_a^1$ is acyl, $R_a^3$ is protected carboxy, A' is a bond, a group of the formula:

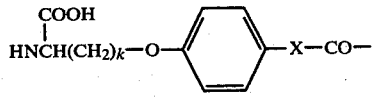

wherein X is a group of the formula:

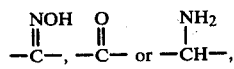

and k is an integer of 1 to 4; or a group of the formula:

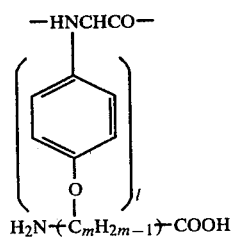

wherein l is an integer of 1 or 0, and m is an integer of 1 to 8, and $R^1$, $R^2$, $R^3$, $R^5$, $R^6$, A and n are as defined above.

Detailed explanation of processes for preparing of the compound (I) will be made in the following:

(1) Process 1: Peptide bond formation Compound (II)+Compound (III)→Compound (Ia)

This process relates to a method for preparing Compound (Ia) by reacting Compound (II) or its salt with a Compound (III) or its salt.

The reaction of this process can be conducted as follows. That is, in one case, as the first step, the carboxy group of Compound (II) or its salt is usually activated in a conventional manner, for example, in the form of its acid halide, azide, acid anhydride or a mixed anhydride, activated ester, and the like, and is reacted with the Compound (III) to give Compound (Ia), and in the other case, the Compound (II) or its salt is reacted with the Compound (III) or its salt directly in the presence of a conventional condensing agent such as N,N-dicyclohexylcarbodiimide and the like. Among these activation methods, preferred activation method for the carboxy group of the Compound (II) into its activated form and preferred condensing agent as mentioned above are selected according to kinds of the carboxy protective group(s) of the Compound (II) and (III) and to the reaction conditions (e.g. the kinds of the reaction solvent, reaction temperature and so on).

This reaction is preferably carried out in a solvent such as methylene chloride, chloroform, tetrahydrofuran, dioxane, ethyl acetate, methanol, ethanol, water or the like under at $-20°$ C. to at ambient temperature and the reaction in the presence of a condensing agent is usually carried out in an anhydrous, but not critical conditions.

(2) Process 2: Selection deacylation Compound (Ib)-→(Ic)

This process relates to a method for preparing Compound (Ic) or its salt by removing selectively an acyl group for $R_a{}^1$ of Compound (Ib) or its salt.

This process is applied to case that the acyl group for $R_a{}^1$ reveals a different chemical property from that of the amino protective group for $R_a{}^4$ against each kind of the removal methods and can selectively be removable by a method to be employed.

This reaction is carried out by conventional methods such as catalytic reduction method, liquidammoniaalkalimetal method, acid method, zinc acid method, base method, hydrazine method and the like. Among these methods, preferred one is selected according to kind of the acyl group for $R_a{}^1$ of Compound (Ib).

Each of the above methods is explained as follows.

(i) Catalytic reduction method:

This method is preferably applied to case that the acyl group for $R_a{}^1$ of Compound (Ib) are one which is removable by catalytic reduction. As preferred examples of such an acyl group for $R_a{}^1$, there may be exemplified substituted or unsubstituted aralkoxycarbonyl (e.g. benzyloxycarbonyl, p-phenylazobenzyloxycarbonyl, p-(p'-methoxyphenylazo)benzyloxycarbonyl, o-nitrobenzyloxycarbonyl, etc.); substituted or unsubstituted alkenyl- or alkynyloxycarbonyl (e.g. allyloxycarbonyl, 1,1-dimethylproparglyloxycarbonyl, etc.); substituted or unsubstituted aryloxyalkanoyl (e.g. 2-nitrophenoxyacetyl, 2-methyl-2-(2-nitrophenoxy)propionyl, etc.); and the like.

This catalytic reduction is carried out in a conventional manner, and suitable catalysts to be used in catalytic reduction are conventional ones such as platinum catalyst (e.g. platinum plate, spongy platinum, platinum black, colloidal platinum, platinum oxide or platinum wire, etc.), palladium catalyst (e.g. spongy palladium, palladium black, palladium oxide, palladium on carbon, colloidal palladium, palladium on barium sulfate, palladium on barium carbonate, etc.), nickel catalyst (e.g. reduced nickel, nickel oxide, Raney nickel, etc.), cobalt catalyst (e.g. reduced cobalt, Raney cobalt, etc.), iron catalyst (e.g. reduced iron, Raney iron, etc.), copper catalyst (e.g. reduced copper, Raney copper, Ullman copper, etc.) or the like.

The reduction is usually carried out in a solvent. A suitable solvent to be used may be, e.g. water, methanol, ethanol, propanol, ethyl acetate, tetrahydrofuran, dioxane, N,N-dimethylformamide, acetic acid, a mixture of water and alcohol (e.g. methanol, ethanol, etc.) tetrahydrofuran, dioxane or ethyl acetate, and other conventional organic solvent or a mixture thereof. Further, the reduction is preferably carried out in the presence of an acid such as acetic acid or the like.

The reaction is preferably carried out under somewhat milder conditions such as cooling or warming.

In this method, in case that $R^7$ is a group of the formula: —CONHNHY and an amino protective group for Y is the same as the acyl for $R_a{}^1$, then such an amino protective group also is simultaneously removed to give a Compound (Ic) wherein $R^7$ is a group of the formula: —CONHNH$_2$. Further, in case that a protected carboxy group for $R^3$ is, for example, substituted or unsubstituted aralkyl ester type one (e.g. benzyl ester p-nitrobenzyl ester, p-chlorobenzyl ester, p-phenylazobenzyl ester, etc.), such a protective group also is simultaneously removed in this process to give a Compound (IC) wherein $R^3$ is carboxy.

(ii) Acid method:

(ii)-1 Method of use of trifluoroacetic acid or formic acid:

This method is preferably applied to case that the acyl group for $R_a{}^1$ is one which is removable by treating with trifluoro-acetic acid or formic acid. Preferred examples of such an acyl group may be exemplified by a group such as branched- or alicyclicoxycarbonyl, (e.g. t-butoxycarbonyl, t-pentoxycarbonyl, t-amyloxycarbonyl, adamantyloxycarbonyl, isobornyloxycarbonyl, etc.); substituted or unsubstituted aralkoxycarbonyl (e.g. p-methoxybenzyloxycarbonyl, etc.).

This reaction is conventionally carried out in a solvent such as methylene chloride, chloroform, acetic acid, water and the like in the presence of trifluoroacetic acid or formic acid, and anisole is preferably added thereto.

Trifluoroacetic acid and formic acid are also used as the solvent.

This reaction is usually carried out under ice-cooling to at ambient temperature.

In this method, in case that $R^7$ is a group of the formula: —CONHNHY and an amino protective group for Y is the same as the acyl for $R_a{}^1$, then such an amino protective group also is simultaneously removed to give a Compound (Ic) wherein $R^7$ is a group of the formula: —CONHNH$_2$. Further, in case that a protected carboxy group for $R^3$ is, for example, a branched alkyl ester (e.g. t-butyl ester, etc.), or substituted or unsubstituted aralkyl ester (e.g. diphenylmethyl ester, p-methoxybenzyl ester, etc.), such a protective group also is simultaneously removed to give a Compound (Ic) wherein $R^3$ is carboxy.

(ii)-2 Method of use of hydrochloric acid or p-toluenesulfonic acid:

This method is preferably applied to case that an acyl group for $R_a{}^1$ is one which is removed by treating with hydrochloric acid or p-toluenesulfonic acid.

Preferred examples of such an acyl group may be exemplified by e.g. substituted or unsubstituted branched alkoxycarbonyl (e.g. t-butoxycarbonyl, 1-(p-biphenyl)-1-methylethoxycarbonyl, etc.) and the like in addition to one as illustrated in the above ii)-1.

This reaction is carried out in a solvent such as ethyl acetate, methylene chloride, chloroform, tetrahydrofuran and the like in the presence of an inorganic or organic strong acid such as hydrochloric acid, p-toluenesulfonic acid or the like, and anisole is preferably added thereto.

This reaction is preferably carried out under ice-cooling to at ambient temperature.

In this method, in case that $R^7$ is a group of the formula: —CONHNHY and an amino protective group for Y is the same as the acyl for $R_a^1$, then such an amino protective group also is simultaneously removed to give a Compound (Ic) wherein $R^7$ is a group of the formula: —CONHNH$_2$. Further, in case that a protected carboxy group for $R^3$ is, for example, a branched alkyl ester (e.g. t-butyl ester etc.) or substituted or unsubstituted aralkyl ester (e.g. diphenylmethyl ester, p-methoxybenzyl ester, etc.), such a protective group also is simultaneously removed to give a Compound (Ic) wherein $R^3$ is carboxy.

(ii)-3 Method of use of hydrogen bromide:

This method is preferably applied to case that an acyl group for $R_a^1$ is one which is removable by treating with hydrogen bromide.

Preferred examples of such an acyl group may be exemplified by substituted or unsubstituted aralkoxycarbonyl (e.g. benzyloxycarbonyl, p-chlorobenzyloxycarbonyl, p-bromobenzyloxycarbonyl, p-tolyloxycarbonyl, p-phenylazobenzyloxycarbonyl, α-naphthylmethoxycarbonyl, etc.) and an alkoxycarbonyl (e.g. isopropoxycarbonyl, etc.) in addition to one as illustrated in the above (ii)-1 and (ii)-2.

This reaction is usually carried out in a solvent such as ethyl acetate, acetic acid, trifluoroacetic acid or the like in the presence of hydrogen bromide.

This reaction is preferably carried out under ice-cooling to at ambient temperature.

In this method, in case that $R^7$ is a group of the formula: —CONHNHY and an amino protective group for Y is the same as the acyl for $R_a^1$, then such an amino protective group also is simultaneously removed to give Compound (I$^c$) wherein $R^7$ is a group of the formula: —CONHNH$_2$. Further, in case that a protected carboxy group for $R^3$ is, for example, a branched alkyl ester or (e.g. t-butyl ester, etc.), substituted or unsubstituted aralkyl ester (e.g. diphenylmethyl ester, p-methoxybenzyl ester, etc.), such a protective group is simultaneously removed to give a Compound (I$^c$) wherein $R^3$ is carboxy.

(iii) Liquid-ammonia-alkali metal method:

This method is preferably applied to case that the acyl group for $R_a^1$ is one which is removable by treating with liquid ammonia-alkali metal. As preferred examples of such an acyl group, there may be exemplified substituted or unsubstituted aralkoxycarbonyl (e.g. benzyloxycarbonyl, etc.), substituted or unsubstituted aryloxycarbonyl (e.g. phenoxycarbonyl, p-methylphenoxycarbonyl, etc.), an arenesulfonyl (e.g. benzenesulfonyl, p-toluenesulfonyl, etc.) and the like.

This reaction is usually carried out by dissolving Compound (I$^b$) into liquid ammonia and then alkali metal is added thereto.

This reaction is preferably carried out at a lower temperature, e.g. at −78° C. to at boiling point of liquid ammonia.

In this method, in case that $R^7$ is a group of the formula: —CONHNHY and amino protective group for Y is the same as the acyl for $R_a^1$, the such an amino protective group also is simultaneously removed to give a Compound (Ic) wherein $R^7$ is a group of the formula: —CONHNH$_2$.

(iv) Hydrazine method:

This method is preferably applied to case that the acyl group for $R_a^1$ is one which is removable by treating with a hydrazine compound or an amine compound. As preferred examples of such an acyl group, there may be exemplified phthaloyl, formyl, acetoacetyl, etc.

Preferred examples of hydrazine compound are exemplified by hydrazine, methylhydrazine, phenylhydrazine and the like and those of amine compound are exemplified by hydroxylamine, dialkylaminoalkylamine (e.g. N,N-dimethylaminopropylamine, etc.) and the like.

This reaction is usually carried out by treating Compound (Ib) with the hydrazine compound or amine compound in a solvent such as water, alcohol (e.g. methanol, ethanol, etc.) tetrahydrofuran, dioxane or the like at ambient temperature to under reflux.

In this method, in case that $R^7$ is a group of the formula: —CONHNHY and an amino protective group for Y is the same as the acyl for $R_a^1$, then such an amino protective group also is simultaneously removed to give a Compound (Ic) wherein $R^7$ is a group of the formula: —CONHNH$_2$.

(v) Zinc-acid method:

This method is preferably applied to case that the acyl group for $R_a^1$ is one which is removable by treating with zinc acid. As preferred examples of such an acyl group, there may be exemplified trichloroethoxycarbonyl, 4-piperidyloxycarbonyl, 1-methyl-1-(4-pyridyl)ethoxycarbonyl and the like.

This method is carried out by treating Compound (Ib) with zinc in the presence of a weak acid such as formic acid, acetic acid and the like. The reaction may be carried out in a solvent such as methylene chloride, chloroform, tetrahydrofuran, ethyl acetate, alcohol (e.g. methanol, ethanol, etc.), dimethylformamide and the like, and in this case a weak acid as mentioned above is added to such a solvent. The reaction is usually carried out at −10° C. to ambient temperature.

In this reaction, in case that $R^7$ is a group of the formula: —CONHNHY and an amino protective group for Y is the same as the acyl for $R_a^1$, then such an amino protective group also is simultaneously removed to give a Compound (Ic) wherein $R^7$ is a group of the formula: —CONHNH$_2$. Further, in case that a protected carboxy group for $R^3$ of Compound (Ib) is, for example, a halo-alkyl ester type of group (e.g. trichloroethyl, etc.), sych a carboxy protective group also is simultaneously removed to give a Compound (Ic) wherein $R^3$ is carboxy.

(vi) Base method:

This method is preferably applied to case that the acyl group for $R_a^1$ is one which is removable by treating with a base. As preferred examples of such an acyl group, there may be exemplified haloalkanoyl (e.g. trifluoroacetyl, etc.), substituted or unsubstituted alkoxycarbonyl (e.g. 2-(p-toluenesulfonyl)ethoxycarbonyl, 2-(p-tolylthio)ethoxycarbonyl, etc.), substituted or unsubstituted aryloxycarbonyl (e.g. 2-nitrophenoxycarbonyl, etc.) and the like.

This method is carried out in the presence of a base under ice-cooling to at ambient temperature.

Suitable base is an inorganic base such as alkali metal hydroxide or alkaline earth metal hydroxide, or the corresponding carbonate or bicarbonate (e.g. sodium hydroxide, potassium hydroxide, sodium carbonate, potassium carbonate, lithium carbonate, sodium bicarbonate, calcium hydroxide, magnesium hydroxide, etc.), ammonium hydroxide or the like; an organic base such as an alkoxide or phenoxide of the above metal (e.g. sodium ethoxide, sodium methoxide, lithium phenoxide, etc.), an amine such as mono-, di- or trialkylamine (e.g. methylamine, ethylamine, propylamine, isopropylamine, butylamine, N,N-dimethyl-1, 3-propanediamine, trimethylamine, triethylamine, etc.), unsubstituted, mono- or disubstituted arylamine (e.g. aniline, N-methylaniline N,N-dimethylaniline, etc.), a heterocyclic base (e.g. pyrrolidine, morpholine, N-methylmorpholine, N-methylpiperidine, N,N-dimethylpiperazine, pyridine, etc.) or the like; a basic ion exchange resin and the like.

This method is preferably conducted under somewhat milder conditions such as coolind or warming and usually in any solvent which does not have an adverse influence on the reaction, e.g. water, a hydrophilic solvent such as alcohol (e.g. methanol, ethanol, propanol, etc.), N,N-dimethylformamide, tetrahydrofuran, dioxane, dimethylsulfoxide, etc. or a mixture thereof. In case that the above-mentioned bases are in liquid, they can also be used as a solvent.

In this method, in case that $R^7$ is a group of the formula: —CONHNHY and an amino protective group for Y is the same as the acyl for $R_a^1$, then such an amino protective group also is simultaneously removed to give a Compound (Ic) wherein $R^7$ is a group of the formula: —CONHNH$_2$. Further, in case that a protected carboxy group for $R^3$ of Compound (Ib) is, for example, an alkyl ester type of group (e.g. methyl ester, ethyl ester, etc.), an aralkyl ester type group (e.g. benzyl ester, etc.), such a protective group also is simultaneously removed to give a Compound (Ic) wherein $R^3$ is carboxy.

(3) Process 3:

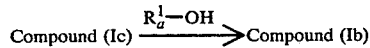

Compound (Ic) $\xrightarrow{R_a^1—OH}$ Compound (Ib)

This process relates to a method for preparing Compound (Ib) by reacting Compound (Ic) with an acylating agent.

The acylating agent to be used in this reaction includes an organic acid ($R_a^1$—OH wherein $R_a^1$ is acyl group) such as monobasic or dibasic organic carboxylic acid, an organic carbonic acid or an organic carbamic acid and the corresponding thio acid or imidic acid; and an organic sulfonic acid, and more particularly, aliphatic, aromatic or heterocyclic carboxylic acid; and the corresponding carbonic, carbamic, thiocarboxylic, thiocarbonic, thiocarbamic, carboximidic, carbamimidic acid, and sulfonic acid; their reactive derivatives; and also includes an isocyanate (e.g. potassium-, alkyl- or aryl-isocyanate), isothiocyanate (e.g. alkyl isothiocyanate) and an isothiourea (e.g. ethyl isothiourea). Suitable examples of these organic acid ($R_a^1$—OH wherein $R_a^1$ is acyl group) are the corresponding organic acid to those comprising the acyl group as exemplified hereinabove in details in the descriptions of suitable examples of acyl groups for $R^1$ and $R_a^1$ of the compound (I).

Said organic acid as an acylating agent can be used in the form of an activated organic acid, i.e. as a reactive derivative of the acid. As such reactive derivatives of said organic acids, there may be exemplified an acid halide, an acid azide, an acid anhydride, an activated amide, an activated ester, etc., and additionally isocyanate and isothiocyanate can preferably be used as reactive derivative of carbamic and thiocarbamic acids, respectively. Preferred examples of such reactive derivatives are illustrated by:

an acid halide (e.g. acid chloride, acid bromide etc.);
an acid azide;
an acid anhydride including a mixed acid anhydride with an acid such as dialkylphosphoric acid, phenylphosphoric acid, diphenylphosphoric acid, dibenzylphosphoric acid, halogenated phosphoric acid, dialkylphosphorous acid, sulfurous acid, thiosulfuric acid, sulfuric acid, monoalkylcarbonic acid, aliphatic carboxylic acid (e.g. acetic acid, pivalic acid, pentanoic acid, isopentanoic acid, 2-ethylbutyric acid, trichloroacetic acid, etc.), aromatic carboxylic acid (e.g. benzoic acid, etc.) or the like, and symmetrical acid anhydride;

an activated amide with pyrazole, imidazole, 4-substituted imidazole, dimethylpyrazole, triazole or tetrazole; and an activated ester such as substituted or unsubstituted alkylthio ester (e.g. methythio ester, carboxymethyl thioester, etc.), substituted or unsubstituted aryl thioester (e.g. phenyl thioester, p-nitrophenyl thioester, p-cresyl thioester, etc.), heterocyclic ester (e.g. pyranyl ester, pyridyl ester, piperidyl ester, 8-quinolyl thioester, etc.) or ester with N,N-dimethylhydroxylamine, 1-hydroxy-2-(1H)-pyridone, N-hydroxysuccinimide, N-hydroxyphthalimide or 1-hydroxy-6-chlorobenzotriazole, or the like.

The above reactive derivative is selected according to the kind of the acid to be used.

In the reaction, when free acid is used as an acylating agent, the acylation reaction may preferably be conducted in the presence of a condensing agent such as carbodiimidic compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus compound (e.g. phosphorus oxychloride, phosphorus trichloride, etc.), thionyl chloride, oxalyl chloride, 2-ethyl-7-hydroxybenzisoxazolium salt, 2-ethyl-5-(m-sulfophenyl)isoxazolium hydroxide, (chloromethylene)dimethylammonium chloride,2,2,4,4,6,6,-hexachloro-1,3,5,2,4,6-triazatriphosphorine, 1-benzenesulphonyloxy-6-chloro-1H-benzotriazole, p-toluenesulfonyl chloride, isopropoxybenzenesulfonyl chloride or the like; or a mixed condensing agent such as a mixture of triphenylphosphine and a carbon tetrahalide (e.g. carbon tetrachloride, carbon tetrabromide, etc.), a complex of N,N-dimethylformamide with phosphoryl chloride, phosgene or thionyl chloride, etc., or the like.

The reaction is usually conducted in a solvent such as water, alcohol (e.g. methanol, ethanol, propanol, etc.), acetone, ethyl ether, dioxane, acetonitrile, ethylacetate, N,N-dimethylformamide, dimethylsulfoxide, tetrahydrofuran, dichloromethane, chloroform, etc. or pyridine, N-methylmorpholine, N-methylpyrrolidine or other conventional solvents, or a mixture thereof. The reaction can also be conducted preferably in the presence of an organic or inorganic base such as alkali metal (e.g. sodium, potassium, etc.), alkaline earth metal (e.g. calcium, etc.), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate, lithium carbonate, etc.), alkali or alkaline earth metal alkoxide (e.g. sodium ethoxide, lithium methoxide, magnesium methoxide, etc.), trialkylamine (e.g. triethylamine, etc.), pyridine, bicyclodiaza compound (e.g. 1,5-diazabicyclo[3,4,0]nonene-5, 1,5-diazabicyclo[5,4,0]undecene-5, etc.) or the like. Among said base, a liquid one can also be used as a solvent.

There is no limination to this reaction temperature, and this reaction may preferably be conducted within the range of cooling to ambient temperature.

(4) Process 4: Elimination of protective group(s)
Compound ($I^d$)→Compound ($I^f$)

This process relates to a method for preparing Compound ($I^e$) or its salt by subjecting Compound ($I^d$) or its salt to elimination reaction of protective group(s) of protected carboxy for $R_a^3$ and $R^7$ and (or) amino protective group for $R_a^4$ and $X^1$, detailed explanation for which is as follows:

Process 4-1: Elimination of an amino protective group for $R_a^4$ and $X^1$

This process can be applied to case that the amino protective group for $R_a^4$ and $X^1$ reveals a chemically different behavior from that of the acyl group for $R^1$ against each kind of the elimination methods to be employed, that is, the case that the amino protective group can be eliminated, but the acyl group for $R^1$ is not eliminated according to the elimination method as employed.

This reaction is carried out by conventional methods such as catalytic reduction method, liquidammoniaalkalimetal method, acid method, zinc acid method, base method, hydrazine method and the like. Among these methods, preferred one is selected according to kind of the amino protective group for $R_a^4$ and $X^1$ also to the chemically different behavior of said amino protective group from the acyl for $R^1$ as explained above.

This reaction is carried out substantially in the same manner as that of Process 2.

Among the above elimination methods, an acid method is employed as the most convenient and conventional one.

Process 4-2: Elimination of carboxy protective group of protected carboxy for $R_a^3$, $R^6$ and $R^7$ The reaction for elimination of protective group of the protected carboxy group is carried out by a conventional method such as hydrolysis and reduction or the like, details of which are explained in the following.

(i) For hydrolysis which refers to the same meaning as solvolysis including, for example, acidolysis, alcoholysis, aminolysis, hydroxinolysis, etc.:

Hydrolysis is preferably carried out in the presence of an acid or base.

Suitable acid includes an inorganic acid (e.g. hydrochloric acid, hydrobromic acid, sulfuric acid, etc.), an organic acid (e.g. formic acid, acetic acid, trifluoroacetic acid, propionic acid, benzenesulfonic acid, p-toluenesulfonic acid, etc.), an acidic ion exchange resin and the like.

Suitable base includes an inorganic base such as alkali or alkaline earth metal hydroxide or the corresponding carbonate or bicarbonate (e.g. sodium hydroxide, potassium hydroxide, sodium carbonate, potassium carbonate, lithium carbonate, sodium bicarbonate, calcium hydroxide, magnesium hydroxide, etc.), ammonium hydroxide or the like; an organic base such as an alkoxide or phenoxide of the above metal (e.g. sodium ethoxide, sodium methoxide, lithium phenoxide, etc.), an amine such as mono-, di- or trialkylamine (e.g. methylamine, ethylamine, propylamine, isopropylamine, butylamine, N,N-dimethyl-1,3-propanediamine, trimethylamine, triethylamine, etc.), unsubstituted mono- or disubstituted arylamine (e.g. aniline, N-methylaniline, N,N-dimethylaniline, etc.), a heterocyclic base (e.g. pyrrolidine, morpholine, N-methylmorpholine, N-methylpiperidine, N,N-dimethylpiperazine, pyridine, etc.), hydrazines (e.g. hydrazine, methylhydrazine, ethylhydrazine, etc.) or the like; a basic ion-exchange resin and the like.

The hydrolysis is preferably conducted under somewhat milder conditions such as cooling or warming and usually in a solvent which does not have adverse influence to the reaction, e.g. water, a hydrophilic solvent such as alcohol (e.g. methanol, ethanol, propanol, etc.), acetone, N,N-dimethylformamide, tetrahydrofuran, dioxane, dimethylsulfoxide, etc. or a mixture thereof, and other hydrophobic solvent such as benzene, diethylether, etc. may also be used as a solvent. A liquid abovementioned acid or base can also be used as solvent.

(ii) For reduction:

Reduction, including chemical reduction and catalytic reduction, is carried out in a conventional manner.

Suitable reducing agents to be used in chemical reduction are a metal (e.g. tin, zinc, iron, etc.), or a combination of such metal and/or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide or platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) or the like.

The reduction is usually carried out in a solvent. A suitable solvent to be used may be e.g. water, alcohol (e.g. methanol, ethanol, propanol, etc.) and other conventional organic solvent or a mixture thereof. Additionally, the afore-mentioned liquid acids to be used in chemical reduction can also be used as solvent. Further, a suitable solvent to be used in catalytic reduction may be, e.g. the above-mentioned solvent, and other conventional solvent, such as diethyl ether, dioxane, tetrahydrofuran etc., or a mixture thereof.

The reaction is preferably carried out under somewhat milder conditions such as cooling or warming.

Process 4-3: Removal of hydrozino group

A protective group of a protected carbazoyl of the formula: —CONHNHY (wherein Y is hydrogen or an amino protective group) can be removed by subjecting Compound (Id) at first to the reaction of Process 4-1 for eliminating an amino protective group (i.e. Y) to give —CONHNH$_2$ group and then subjecting the reaction product to the reaction of this step to give —COOH group, and particular of this reaction step is as follow.

The reaction of this step is carried out in a conventional manner by treating the Compound (Id) with a conventional oxidizing agent which is capable of oxidizing a group of the formula: —CONHNH$_2$ to form into a group of the formula: —COOH and accordingly preferred example of such an oxidizing agents may be halogen such as iodine, bromine etc., perhalogenic acid such as periodic acid or its salt (e.g. sodium salt, potassium salt, etc.), perchloric acid, etc., N-haloimide such as N-bromosuccinimide, etc., lead tetraacetate, hydrogen peroxide or its salt (e.g. nickel peroxide, etc.), metal oxide such as mercuric oxide, manganese dioxide, nickel peroxide, etc., cupric compound (e.g. cupric acetate, cupric sulfate, etc.) and the like.

This reaction is usually carried out in a solvent such as water, acetic acid, methanol, ethanol, tetrahydrofuran, dioxane and the like and a mixture thereof, which should be appropriately selected in accordance with the kind of oxidizing agent to be used.

This reaction is usually carried out under ice-cooling to at ambient temperature, or under reflux.

Among these methods for elimination of protective groups, preferred one and appropriate combination methods are to be selected according to kinds of the protective groups of carboxy group and amino protective group to be removed off.

It is noted that this process includes the following cases of elimination of protective groups of protected carboxy and amino protective group, that is, one case that all of the carboxy protective groups for $R_a^3$, $R_b^4$ and $R^6$ and the amino protective group for $R_a^4$ in the Compound ($I^d$) are simultaneously removed by a method to be employed to the reaction, and the other case that the carboxy protective groups and the amino protective group are sequentially and stepwise removed by a method which is appropriately selected according to the kinds of the protective group to be removed.

As to Process 4 for elimination of protective group(s) (i.e. Process 4-1 and 4-2 and 4-3), the followings are to be noted. That is, in case that acyl for $R^1$ has one or more protective group(s) for hydroxy, amino and (or) carboxy, such as amino protective group and carboxy protective group among said protective group may be simultaneously removed in this process, and such a hydroxy protective group such as alkanoyl (e.g. acetyl, etc.) may be previously removed by subjecting the compound ($I^d$) to elimination reaction of hydroxy protective group in a conventional manner such as reduction as illustrated in the Process 2.

(5) Process 5: Reduction

This process relates to a method for preparing a compound ($I^g$) or its salt by reducing a compound ($I^f$) or its salt.

The reaction of this process is carried out substantially in the same manner as that of Process 4-2.

The starting Compounds (II) and (III) include known compounds (e.g. European Patent publication No. 11283) and new compounds. Said new compounds can be prepared, for example, by methods as described below.

(1) Process 1$^s$:

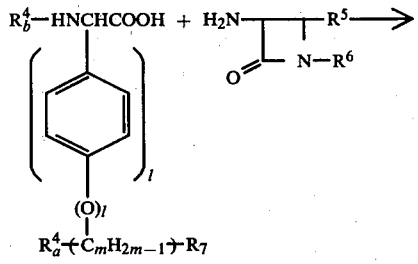

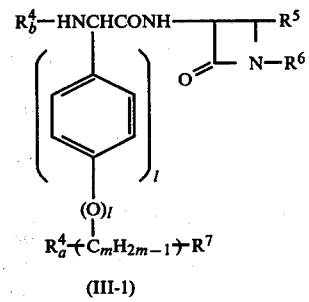

(2) Process 2$^s$:

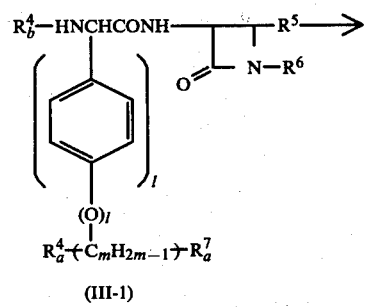

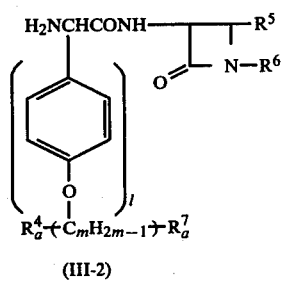

In the above formulae, $R_b^4$ is an amino protective group and $R_a^7$ is protected carboxy, and l, m, $R^5$ and $R^6$ are each as defined above.

(1) Process 1$^s$: Compound (IV)+Compound (V)→Compound (III-1)

This process relates to a method for preparing Compound (III-1) or its salt by reacting Compound (IV) or its salt with Compound (V) or its salt.

The reaction is carried out substantially in the same manner as Process 1.

(2) Process 2$^s$: Compound (III-1)→Compound (III-2)

This process relates to a method for preparing Compound (III-2) or its salt by subjecting Compound (III-1) or its salt to elimination reaction of protective group(s).

The reaction is carried out substantially in the same manner as Process 2.

As to the object compound (I) and starting compounds (II) and (III) which are prepared according to the aforementioned Processes, it is to be noted that each of said compounds includes one or more stereoisomers which is due to the asymmetric carbon atoms in their molecule and all of such isomers are included within the scope of this invention.

The new peptide (I) and its pharmaceutically acceptable salts of this invention have been found to possess protective efficacy in experimental infection.

Accordingly, the new peptide (I) and its pharmaceutically acceptable salts are useful for the therapeutic treatment of infectious diseases caused by pathogenic microorganism, especially gram-negative bacteria and gram-positive bacteria and fungi.

Further, Compounds (II) and (III) are useful as intermediate for preparing Compound (I) having biologically active properties as mentioned above.

For the purpose of showing pharmaceutical utility of the new peptide (I), pharmacological test data thereof are illustrated in the following.

PROTECTIVE EFFICACY IN EXPERIMENTAL INFECTION IN MICE

In determining the protective efficacy against experimental infections in mice, the test compound was dissolved in and diluted with sterile saline to provide prescribed concentrations of drug.

Male ICR-strain mice, aged 4 weeks were used in groups of ten mice. $E.\ coli$ 22 was cultivated overnight at 37° C. on trypticase soy agar and then were suspended in a sterile saline to obtain microbial cell concentration of $2.6 \times 10^9$ CFU/ml. Mice were inoculated intraperitoneally with $8.7 \times 10^7$ CFU/mouse. Each of the test drugs was given intraperitoneally in various doses to a group of ten mice four days before challenge.

Survival percent were found from the number of the surviving animals after three days of injection. Results are shown in Table.

| Test Compound (Example No.) | Survival (%) Dose (mg/kg) | | | |
|---|---|---|---|---|
| | 1 | 0.1 | 0.01 | 0 |
| 1 (Step 1) | | 100 | 80 | |
| 8 (Step 2) | 60 | 40 | | 30 |
| 15 (Step 2) | 80 | 80 | | 20 |
| 16 (Step 2) | 50 | 30 | 30 | 10 |
| 18 (Step 2) | 50 | 40 | 50 | 30 |
| 19 (Step 2) | 50 | 50 | 60 | 30 |
| 20 (Step 2) | 60 | 90 | 60 | 30 |
| 21 (Step 3) | 80 | 60 | 10 | 10 |

The pharmaceutical composition of this invention can be used in the form of a pharmaceutical preparation, for example, in solid, semisolid or liquid form, which contains an active substance of this invention in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glycose, lactose, gum acacia, gelatin, mannitol, starch paste, magnesium trisilicate, talc, corn starch, keratin, collidal silica, potato starch, urea and other carriers suitable for use in manufacturing preparations, in solid, semisolid, or liquid form, and in addition auxiliary, stabilizing, thickening and coloring agents and perfumes may be used. The pharmaceutical compositions can also contain preservative or bacteriostatic agents to keep the active ingredient in the desired preparations stable in activity. The active object compound is included in the pharmaceutical composition in an amount sufficient to produce the desired therapeutic effect upon the process or condition of diseases.

For applying this composition to humans, it is preferably to apply it by intravenous, intramuscular or oral administration. While the dosage or therapeutically effective amount of the object compound of this invention varies from and also depends upon the age and condition of each individual patient to be treated, a daily dose of about 0.1–100 mg of the active ingredient/kg of a human being or an animal is generally given for treating diseases, and an average single dose of about 50 mg, 100 mg, 250 mg, and 500 mg is generally administered.

The following examples are given for purpose of illustrating this invention.

In the following examples, starting compounds and object compounds are expressed by using the following abbreviations:

| | |
|---|---|
| Et | Ethyl |
| Lac | Lactoyl |
| Ala | Alanyl |
| Glu | Glutamyl |
| Gly | Glycyl |
| DAP | α, ε-Diaminopimelyl |
| Z | benzyloxycarbonyl |
| Boc | t-butoxycarbonyl |
| Bzl | Benzyl |
| Ac | acetyl |
| Su | N—hydroxysuccinimide |

-continued

DL-Nocardicin C
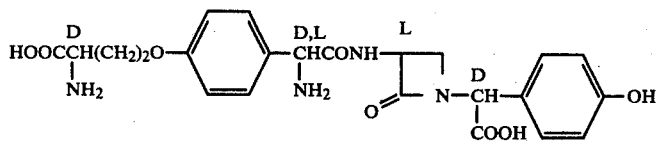

3ANA
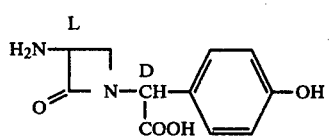

Nocardicin A
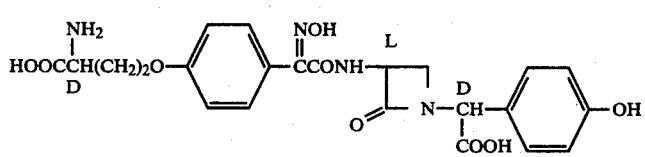

PREPARATION 1

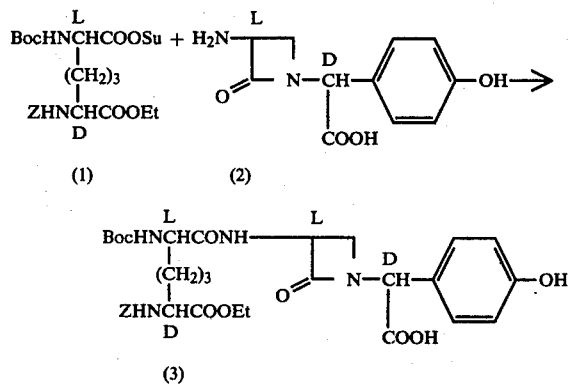

To a mixture of 3ANA (2) (1.18 g) and sodium bicarbonate (0.42 g) in acetone (20 ml) and water (20 ml) was added Boc-(L)-Z-(D)-mesoDAP-(D)-OEt-(L)-OSu (1). The mixture was stirred for 5 hours at room temperature and concentrated. To the residue was added ethyl acetate (50 ml), water (20 ml) and diluted hydrochloric acid (10 ml). The organic layer was separated, washed with water, dried over magnesium sulfate and then evaporated. The residue was pulverized with ethyl acetate (5 ml) and diisopropylether (50 ml) to give Boc-(L)-Z-(D)-mesoDAP-(D)-OEt-(L)-3ANA (3) (2.75 g).

IR (Nujol): 3270, 1715 (broad), 1505 cm$^{-1}$

NMR (CD$_3$OD): δ 1.0–1.9 (9H, m), 1.34 (9H, s), 3.02 (1H, m), 3.5–4.2 (5H, m), 4.88 (1H, m), 4.97 (2H, s), 5.36 (1H, s), 6.89 (4H, ABq, J=8 Hz), 7.23 (5H, s).

PREPARATION 2

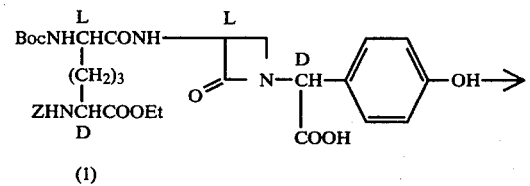

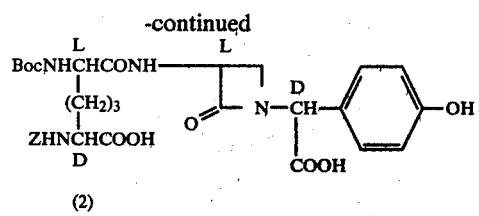

Boc-(L)-Z-(D)-mesoDAP-(D)-OEt-(L)-3ANA (1) (2.7 g) was added to 0.5 N sodium hydroxide (12 ml) under ice-bath cooling and the mixture was stirred for 30 minutes at the same temperature. Diluted hydrochloric acid was added to the reaction mixture with stirring under ice-bath cooling to adjust to pH 2. The mixture was extracted with ethyl acetate and the organic layer was washed with water and dried over magnesium sulfate and evaporated to give an oil, which was pulverized with ethyl acetate (6 ml) and diisopropyl ether (60 ml) to give Boc-(L)-Z-(D)-mesoDAP-(L)-3ANA (2) (2.25 g).

IR (Nujol): 3290, 1705 (broad), 1515 cm$^{-1}$

NMR (CD$_3$OD), δ: 1.2–2.0 (6H, m), 1.37 (9H, s), 3.10 (1H, m), 3.5–4.2 (3H, m), 4.93 (1H, m), 5.03 (2H, s), 5.40 (1H, s), 6.94 (4H, ABq, J=8 Hz), 7.25 (5H, s).

PREPARATION 3

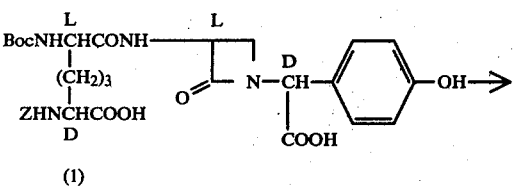

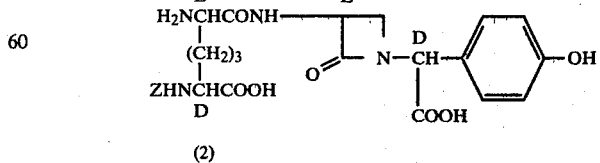

To a suspension of Boc-(L)-Z-(D)-mesoDAP-(L)-3ANA (1) (2.0 g) in benzene (4 ml) and anisole (0.6 ml) was added trifluoroacetic acid, and the mixture was stirred for 10 minutes at 5° C. Ethyl ether (130 ml) was added to the reaction mixture and the resulting precipitates were collected, which was recrystallized from methanol (10 ml) and ether (180 ml) to give Z-(D)-mesoDAP-(L)-3ANA (2) (1.4 g).

IR (Nujol): 3250, 1720, 1675, 1505 cm⁻¹
NMR (CD₃OD), δ: 1.2–2.2 (6H, m), 3.13 (1H, m), 3.5–4.2 (3H, m), 5.08 (2H, s), 5.42 (1H, s), 7.02 (4H, ABq, J=8 Hz), 7.33 (5H, s).

Ala-γ-D-Glu(α-OBzl)-(α)-Boc(ω)-DL-Nocardicin C (3) (870 mg).

IR (Nujol): 3260, 1730, 1650, 1510 cm⁻¹
NMR (CD₃OD), δ: 1.0–1.7 (15H, m), 1.7–2.7 (6H, m), 2.0 (3H, s), 3.12 (1H, m), 3.5–4.7 (7H, m), 5.17 (2H, s), 5.30, 5.33 (two S, 1H), 5.45 (1H, s), 6.7–7.5 (8H, m), 7.35 (5H, s).

(2) Step 2

Compound (3) ⟶

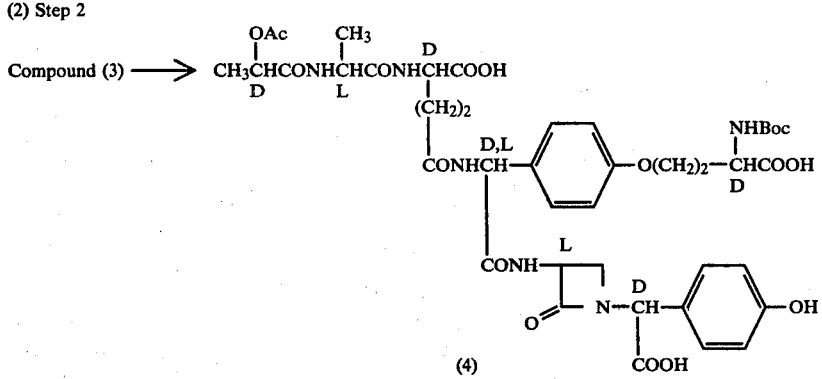

EXAMPLE 1

(1) Step 1

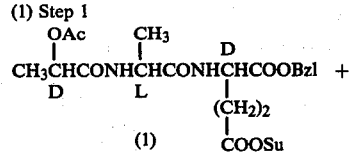

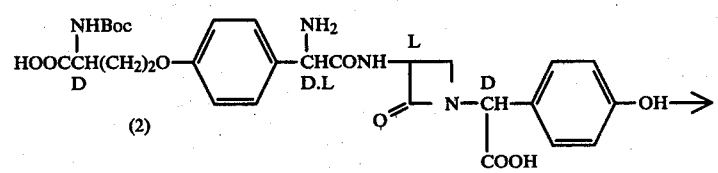

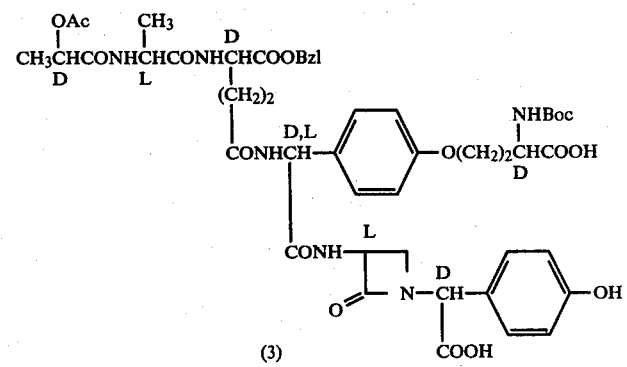

To a mixture of DL-Nocardicin C(ω-Boc) (2) (586 mg) triethylamine (202 mg) in acetone (20 ml) and water (10 ml) was added D-Lac(OAc)-L-Ala-γ-D-Glu(α-OBzl)OSu (1) (570 mg).

The mixture was stirred for 17 hours at room temperature and concentrated. The residue was dissolved in ethyl acetate and the ethyl acetate was washed with diluted hydrochloric acid and water, dried over magnesium sulfate and evaporated to give D-Lac(OAc)-L-Ala-γ-D-Glu(α-OBzl)-(α)-Boc(ω)-DL-Nocardicin C (3) (700 mg) was dissolved in methanol (15 ml) and hydrogenated under 2.5 atmospheric pressure of hydrogen over 10% palladium charcoal (100 mg). After removal of the catalyst, the mixture was concentrated under reduced pressure. The residue was pulverized with ethyl acetate and collected to give D-Lac(OAc)-L-Ala-γ-D-Glu(α-OH)-(α)-Boc(ω)-DL-Nocardicin C (4) (580 mg).

IR (Nujol): 3250, 1720, 1645, 1505 cm⁻¹
NMR (CD₃OD), δ: 1.1–1.6 (15H, m), 1.6–2.5 (6H, m), 2.0 (3H, s), 3.12 (1H, m), 3.76 (1H, m), 4.03 (2H, t, J=6 Hz), 4.1–4.5 (4H, m), 5.24, 5.26 (1H, two S), 5.40 (1H, s), 6.6–7.4 (8H, m).

(3) Step 3

Compound (4) ⟶

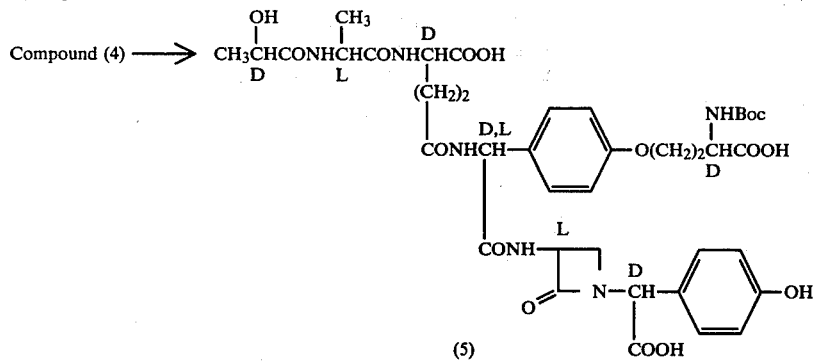

D-Lac(OAc)-L-Ala-γ-D-Glu(α-OH) (α)-Boc(ω)-DL-Nocardicin C (4) (580 mg) and sodium carbonate (350 mg) was dissolved in water (15 ml). The mixture was stirred for 7 hours at room temperature. The reaction mixture was adjusted to pH 2 with diluted hydrochloric acid and extracted with ethyl acetate (150 ml).

The ethyl acetate layer was washed with water, dried over magnesium sulfate and then evaporated to give a foamy residue, which was pulverized with ether to give D-Lac-L-Ala-γ-D-Glu(α-OH)-(α)-Boc(ω)-DL-Nocardicin C (5) (340 mg).

IR (Nujol): 3270, 1725, 1650, 1510 cm$^{-1}$

NMR (CD$_3$OD), δ: 1.41 (9H, s), 1.1–1.5 (6H, m), 1.99 (3H, s), 2.0–2.4 (6H, m), 3.08 (1H, m), 3.76 (1H, m), 3.9–4.4 (6H, m), 5.25, 5.29 (1H, two S), 5.40 (1H, s), 6.6–7.4 (8H, m)

D-Lac-L-Ala-γ-D-Glu(α-OH)-(α)-Boc(ω)-DL-Nocardicin C (5) (340 mg) was suspended in benzene (3 ml), and trifluoroacetic acid (3 ml) was added thereto. The mixture was stirred for 1 hour at 5° C., and ether (20 ml) was added thereto.

The resulting precipitate was subjected to column chromatography of macroporous non-ionic adsorption resin, HP20 (30 ml). The column was eluted with 20% aqueous methanol and fractions containing the object compound (6) were collected and evaporated under reduced pressure to give residues, which were pulverized with acetone to give D-Lac-L-Ala-γ-D-Glu(α-OH)-(α)-DL-Nocardicin C (6) (145 mg).

IR (Nujol): 3250, 1730, 1645, 1510 cm$^{-1}$

NMR (D$_2$O), δ: 1.2–1.5 (6H, m), 1.6–2.6 (6H, m), 3.06 (1H, m), 3.72 (1H, m), 3.9–4.4 (6H, m), 5.29 (1H, s), 5.40 (1H, s), 6.7–7.4 (8H, m).

(4) Step 4

Compound (5) ⟶

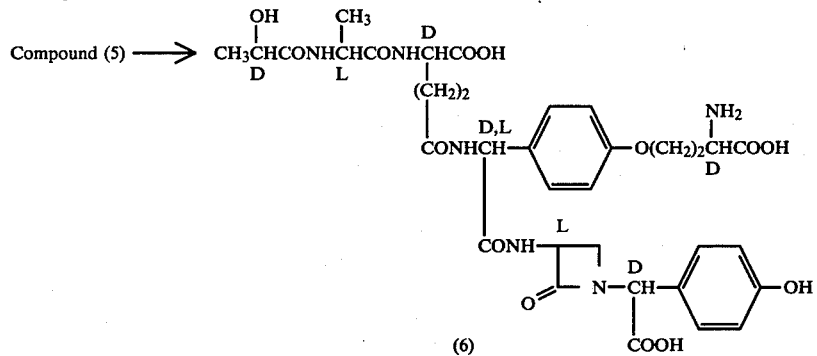

EXAMPLE 2

(1) Step 1

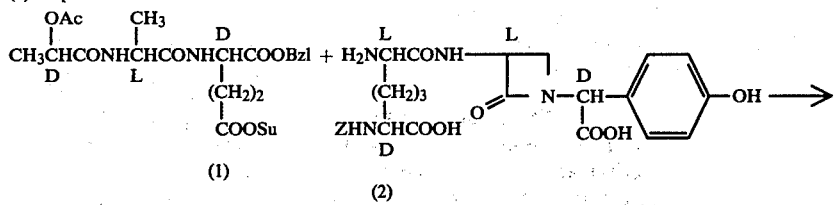

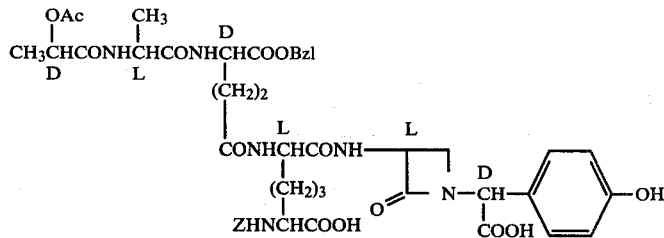

(3)

D-Lac(OAc)-L-Ala-γ-D-Glu(α-OBzl)-(L)-Z-(D)-mesoDAP-(L)-3-ANA (3) was prepared substantially in the same manner as step 1 of Example 1.

IR (Nujol): 3250, 1725, 1650, 1510 cm$^{-1}$

NMR (CD$_3$OD), δ: 1.1–2.0 (6H, m), 1.35 (3H, d, J=6 Hz), 1.43 (3H, d, J=7 Hz), 2.0–2.4 (4H, m), 2.07 (3H, s), 3.17 (1H, m), 3.70 (1H, m), 4.0–4.6 (5H, m), 4.90 (1H, m), 5.07 (2H, s), 5.15 (2H, s), 5.43 (1H, s), 6.97 (4H, ABq, J=8 Hz), 7.32 (10H, s)

0.5 N aqueous sodium hydroxide (8 ml) and the mixture was stirred for 30 minutes at room temperature.

The reaction mixture was adjusted to pH 2 with diluted hydrochloric acid and subjected to column chromatography of HP-20 (30 ml). The column was eluted with water. The fractions containing the object compound (5) were collected and evaporated under reduced pressure to give a foamy residue, which was dissolved in water and lyophilized to give D-Lac-L-Ala-γ-D-Glu(α-OH)-(L)-mesoDAP-(L)-3ANA(5) (350 mg).

IR (Nujol): 3260, 1730, 1645 cm$^{-1}$

NMR (D$_2$O), δ: 1.0–2.5 (10H, m), 1.34 (3H, d, J=7 Hz), 1.38 (3H, d, J=7 Hz), 3.14 (1H, m), 3.6–3.8 (2H, m), 4.0–4.4 (4H, m), 4.86 (1H, m), 5.34 (1H, s), 7.04 (4H, ABq, J=8 Hz)

(2) Step 2

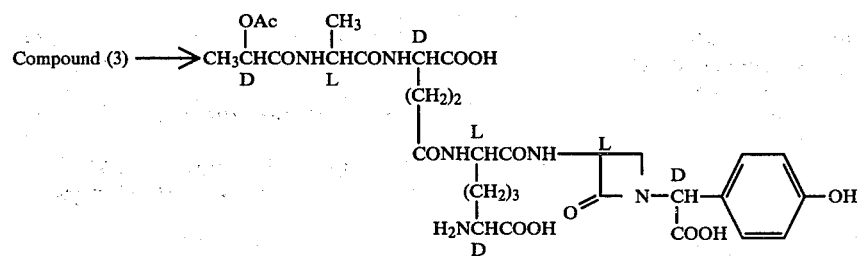

(4)

D-Lac(OAc)-L-Ala-γ-D-Glu(α-OH)-(L)-mesoDAP-(L)-3ANA (4) was prepared substantially in the same manner as step 2 of Example 1.

NMR (CD$_3$OD), δ: 0.9–2.3 (10H, m), 1.38 (3H, d, J=6 Hz), 1.45 (3H, d, J=6 Hz), 2.10 (3H, s), 3.15 (1H, m), 3.5–4.0 (2H, m), 4.1–4.6 (4H, m), 5.40 (1H, s), 7.0 (4H, ABq, J=8 Hz)

(3) Step 3

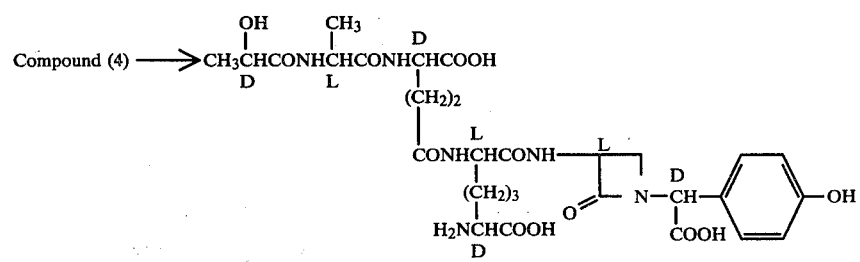

(5)

D-Lac(OAc)-L-Ala-γ-D-Glu(α-OH)-(L)-mesoDAP-(L)-3ANA (4) (500 mg) was dissolved in an ice-cooled

EXAMPLE 3

(1) Step 1
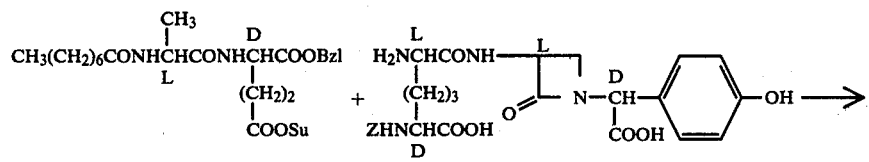
(1)        (2)
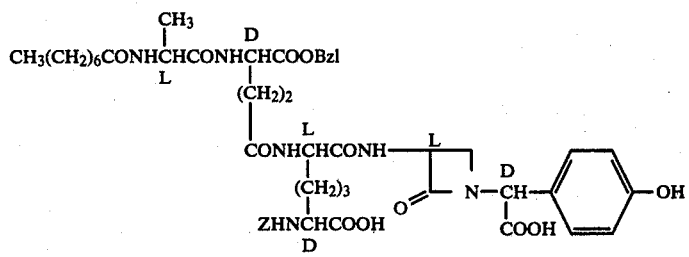
(3)
Octanoyl-L-Ala-γ-D-Glu(α-OBzl)-(L)-Z-(D)-mesoDAP-(L)-3ANA (3) (0.55 g) was prepared substantially in the same manner as step 1 of Example 1.
IR (Nujol): 3250, 1730, 1640, 1520 cm$^{-1}$
NMR (CD$_3$OD), δ: 0.9–1.1 (3H, m), 1.1–2.0 (18H, m), 2.0–2.5 (4H, m), 3.15 (1H, m), 3.80 (1H, m), 4.1–4.7 (4H, m), 5.10 (2H, s), 5.17 (2H, s), 5.47 (1H, s), 7.0 (4H, ABq, J=8 Hz), 7.37 (10H, s).
Octanoyl-L-Ala-γ-D-Glu(α-OH)-(L)-mesoDAP-(L)-3ANA (4) was prepared substantially in the same manner as step 2 of Example 1.
IR (Nujol): 3250, 1730, 1640 (broad), 1530 (broad) cm$^{-1}$
NMR (CD$_3$OD), δ: 0.7–1.0 (3H, m), 1.1–2.1 (22H, m), 3.12 (1H, m), 3.5–3.9 (2H, m), 4.1–4.5 (3H, m), 5.40 (1H, s), 6.96 (4H, ABq, J=8 Hz).
(2) Step 2
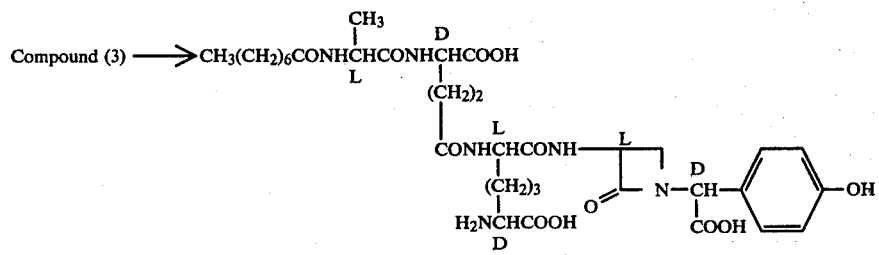
(4)
EXAMPLE 4
(1) Step 1
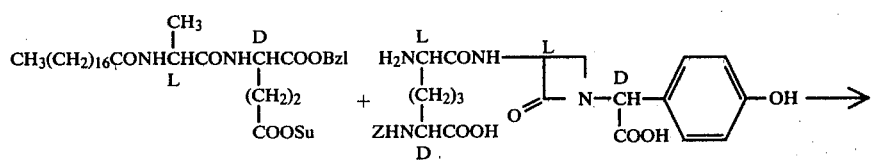
(1)        (2)

(1) Step 1

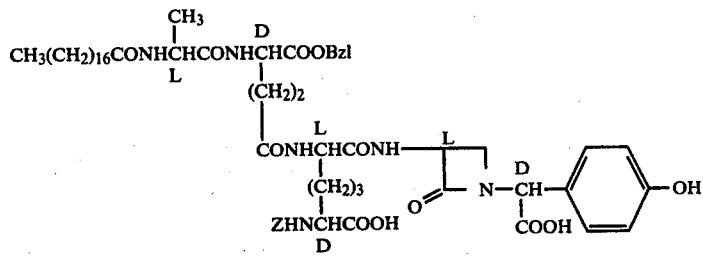

(3)

To a mixture of Z-(D)-mesoDAP-(L)-3ANA (2) (370 mg) and triethylamine (68 mg) in methylene chloride (15 ml) and methanol (1 ml) was added stearoyl-L-Ala-γ-D-Glu(α-OBzl)-OSu (1) (460 mg). The mixture was stirred for 5 hours at room temperature and concentrated.

The residue was dissolved in water and the aqueous layer was adjusted to pH 2 with diluted hydrochloric acid. The resulting precipitate was filtered to give stearoyl-L-Ala-γ-D-Glu(α-OBzl)-(L)-Z-(D)-mesoDAP-(L)-3ANA (3) (250 mg).

IR (Nujol): 3250, 1720, 1630, 1530 cm$^{-1}$

NMR (CD$_3$OD-CDCl$_3$), δ: 0.8–1.1 (3H, m), 1.2–2.0 (38H, m), 2.0–2.5 (4H, m), 3.20 (1H, m), 3.88 (1H, m), 4.1–4.3 (4H, m), 4.97 (1H, m), 5.13 (2H, s), 5.17 (2H, s), 5.52 (1H, s), 7.05 (4H, ABq, J=8 Hz), 7.37 (10H, s).

Stearoyl-L-Ala-γ-D-Glu(α-OBzl)-(L)-Z-(D)-mesoDAP-(L)-3ANA (3) (300 mg) was dissolved in methanol (15 ml) and hydrogenated under 2.5 atmospheric pressure of hydrogen over 10% palladium charcoal (150 mg). After removal of the catalyst, the mixture was evaporated under reduced pressure to give a foamy residue, which was pulverized with acetone to give stearoyl-L-Ala-γ-D-Glu(α-OH)-(L)-mesoDAP-(L)-3ANA (4) (170 mg).

IR (Nujol): 3250, 1735, 1640 (broad), 1530 (broad) cm$^{-1}$

NMR (CD$_3$OD-DMSO-d$_6$), δ: 0.7–1.0 (3H, m), 1.0–2.0 (38H, m), 2.0–2.3 (4H, m), 3.06 (1H, m), 3.52 (1H, m), 3.74 (1H, m), 4.0–4.3 (3H, m), 4.84 (1H, m), 5.28 (1H, s), 6.94 (4H, ABq, J=8 Hz)

(2) Step 2

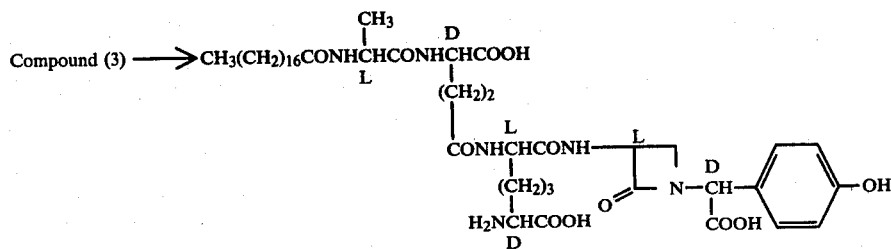

(4)

EXAMPLE 5

(1) Step 1

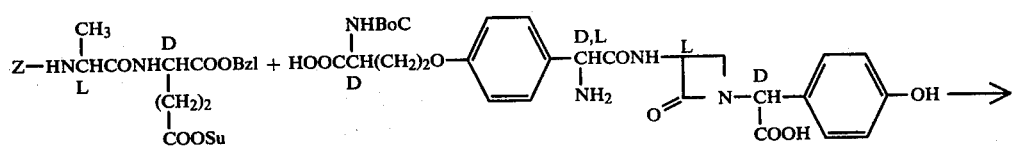

(1)  (2)

-continued (1) Step 1

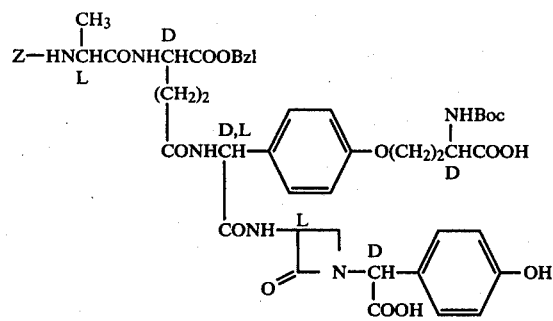

(3)

Z-L-Ala-γ-D-Glu(α-OBzl)-(α)-Boc-(ω)-DL-Nocardicin C (3) was prepared substantially in the same manner as step 1 of Example 1.

IR (Nujol): 3300, 1730, 1700, 1650 cm⁻¹

NMR (CD₃OD), δ: 1.66 (3H, d, J=6 Hz), 1.46–1.70 (2H, m), 1.41 (9H, s), 2.08–2.25 (4H, m), 3.68–3.76 (1H, m), 4.08–4.45 (6H, m), 5.03 (2H, s), 5.13 (2H, s), 5.26 (1H, s), 5.43 (1H, s), 6.70–7.20 (8H, m), 7.30 (5H, s), 7.31 (5H, s).

(2) Step 2

Compound (3) ⟶

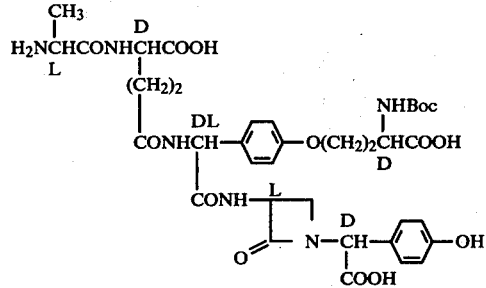

(4)

L-Ala-γ-D-Glu(α-OH)(α)-Boc-(ω)-DL-Nocardicin C (4) was prepared substantially in the same manner as step 2 of Example 1.

IR (Nujol): 3250, 1730, 1680–1650 cm⁻¹

NMR (CD₃OD), δ: 1.41 (9H, s), 1.38–1.56 (5H, m), 2.16–2.41 (4H, m), 3.73–4.43 (7H, m), 5.35 (broad, 2H, s), 6.73–7.38 (8H, m)

(3) Step 3

Compound (4) ⟶

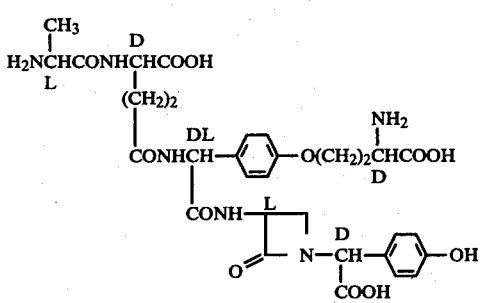

(5)

L-Ala-γ-D-Glu(α-OH)-(α)-DL-Nocardicin C (5) was prepared substantially in the same manner as step 4 of Example 1.

IR (Nujol): 3250, 1730, 1660–1640 cm⁻¹

NMR (DMSO-d₆/D₂O), δ: 1.30–1.46 (5H, m), 2.00–2.30 (4H, m), 3.50–3.58 (1H, m), 5.06 (1H, s), 5.30 (1H, s), 6.66–7.36 (8H, m).

EXAMPLE 6

(1) Step 1

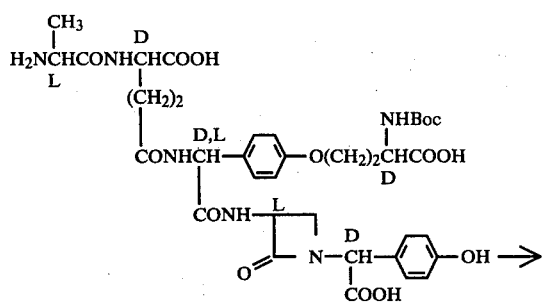

(1)

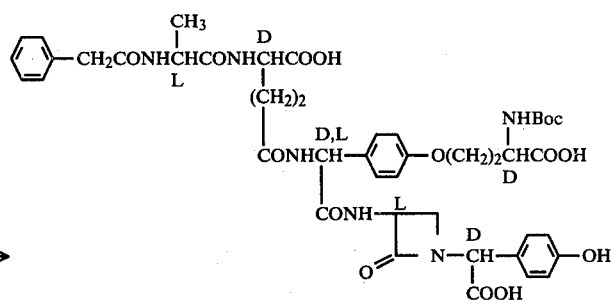

(2)

To a mixture of L-Ala-γ-D-Glu(α-OH)-(α)-Boc-(ω)-DL-Nocardicin C (1) (786 mg) and N-methylmorpholine (404 mg) in acetone (20 ml) and water (10 ml) was added phenylacetyl chloride (220 mg). The mixture was stirred for 1 hour at 0° C., and concentrated.

The residue was dissolved in a mixture of ethyl acetate and diluted hydrochloric acid. The organic layer was washed with water, dried over magnesium sulfate and evaporated to give a foamy residue, which was pulverized with ether to give phenylacetyl-L-Ala-γ-D-Glu(α-OH)-(α)-Boc-(ω)-DL-Nocardicin C (2) (790 mg)

IR (Nujol): 3300, 1730, 1650–1640 cm$^{-1}$

Phenylacetyl-L-Ala-γ-D-Glu(α-OH)-(α)-DL-Nocardicin C (3) was prepared substantially in the same manner as step 4 of Example 1.

IR (Nujol): 3250, 1735, 1660–1640 cm$^{-1}$

NMR (DMSO-d$_6$/D$_2$O), δ: 1.26–1.41 (5H, m), 1.83–2.36 (4H, m), 3.00–3.13 (1H, m), 3.55 (2H, s), 3.70–4.86 (7H, m), 5.26 (1H, s), 5.33 (1H, s), 6.96–7.36 (8H, m). 7.28 (5H, s).

EXAMPLE 7

(2) Step 2

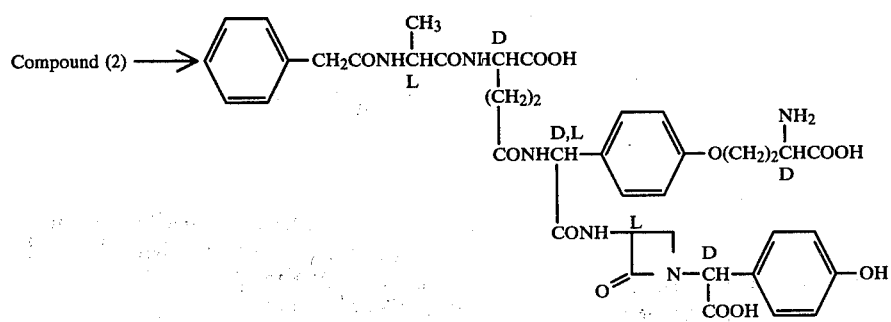

(3)

(1) Step 1

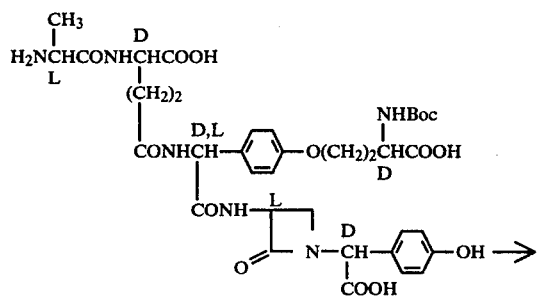

(1)

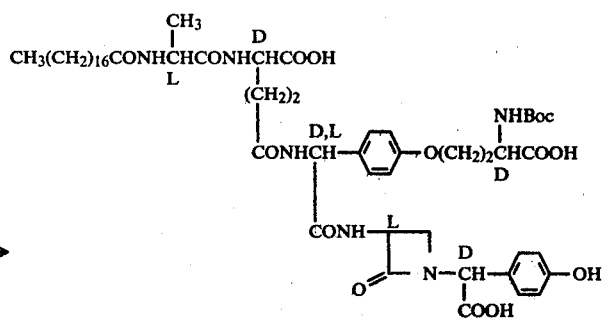

(2)

Stearoyl-L-Ala-γ-D-Glu(α-OH)-(α)-Boc-(ω)-DL-Nocardicin C (2) was prepared substantially in the same manner as step 1 of Example 6
IR (Nujol): 3250, 1720–1730, 1650–1640 cm$^{-1}$ (1) Step 1

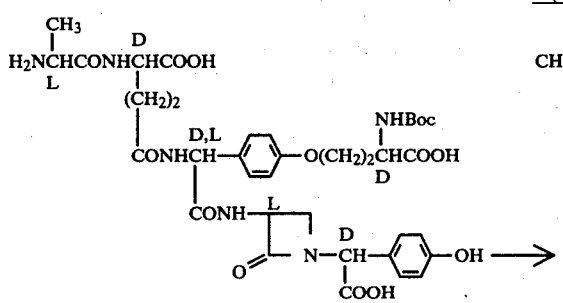

(1)

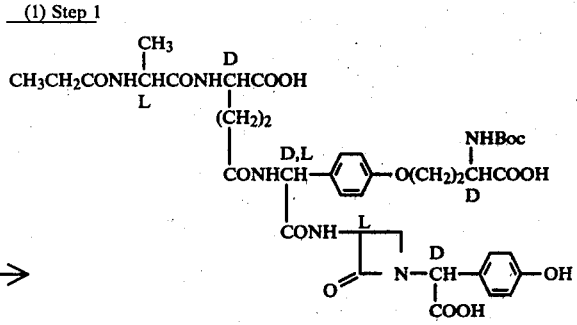

(2)

(2) Step 2

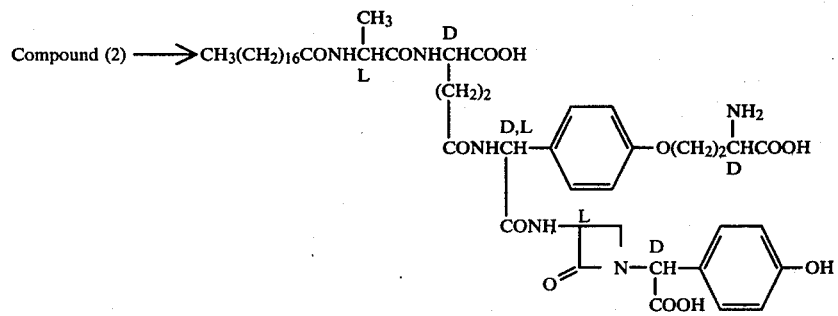

Stearoyl-L-Ala-γ-D-Glu(α-OH)-(α)-DL-Nocardicin C (3) was prepared substantially in the same manner as step 4 of Example 1.
IR (Nujol): 3280, 1735, 1660, 1640 cm$^{-1}$
NMR (DMSO-d$_6$/D$_2$O), δ: 0.86 (3H, t, J=5 Hz), 1.16–1.30 (38H, m), 2.03–2.33 (6H, m), 2.76–3.03 (1H, m), 3.60–4.50 (6H, m), 5.30 (2H, broad s), 6.70–7.36 (8H, m)

EXAMPLE 8

Propionyl-L-Ala-γ-D-Glu(α-OH)(α)-Boc-(ω)-DL-Nocardicin C (2) was prepared substantially in the same manner as step 1 of Example 6.
IR (Nujol): 3300, 1730, 1650 cm$^{-1}$
NMR (CD$_3$OD): δ: 1.13 (3H, t, J=5 Hz), 1.25 (3H, d, J=6 Hz), 1.26 (9H, s), 2.00–2.41 (6H, m), 3.01–3.15 (1H, m), 3.73–4.43 (7H, m), 5.30 (1H, s), 5.46 (1H, s), 6.73–7.40 (8H, m)

(2) Step 2
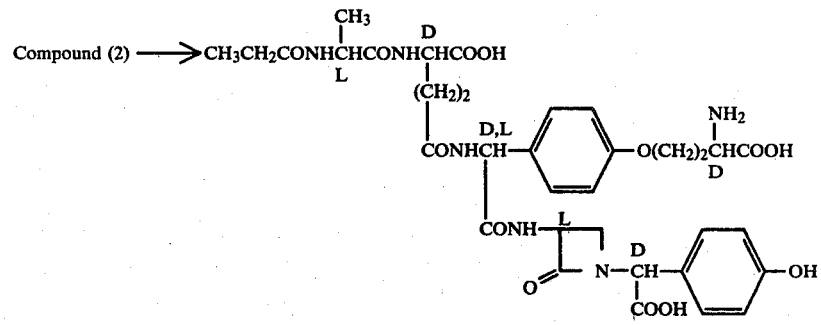
Propionyl-L-Ala-γ-D-Glu(α-OH)-(α)-DL-Nocardicin C (3) was prepared substantially in the same manner as step 4 of Example 1.
IR (Nujol): 3250, 1730, 1650–1630 cm$^{-1}$
NMR (D$_2$O), δ: 1.03 (3H, t, J=6 Hz), 1.33 (3H, d, J=5 Hz), 2.13–2.30 (6H, m), 3.01–3.13 (1H, m), 3.66–4.40 (6H, m), 5.28 (1H, s), 5.40 (1H, s), 6.78–7.36 (8H, s)
Octanoyl-L-Ala-γ-D-Glu(α-OBzl)-(α)-Boc-(ω)-DL-Nocardicin C (3) was prepared substantially in the same manner as step 1 of Example 1.
IR (Nujol): 3280, 1735, 1720, 1645 cm$^{-1}$
NMR (CD$_3$OD), δ: 0.916 (3H, t, J=6 Hz), 1.25–1.66 (15H, m), 1.43 (9H, s), 2.10–2.25 (6H, m), 3.66–4.58 (6H, m), 5.18 (1H, s), 5.20 (2H, s), 5.48 (1H, s), 6.76–7.33 (8H, m), 7.36 (5H, s).
EXAMPLE 9
(1) Step 1
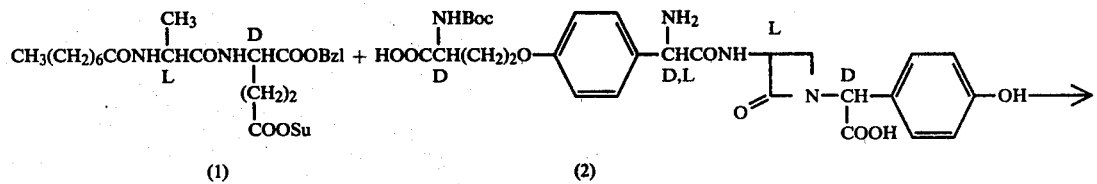
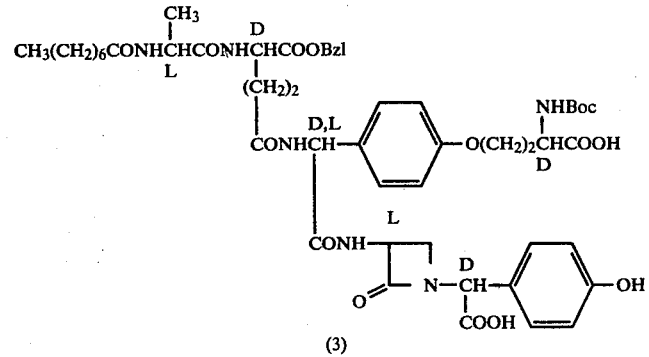
(2) Step 2

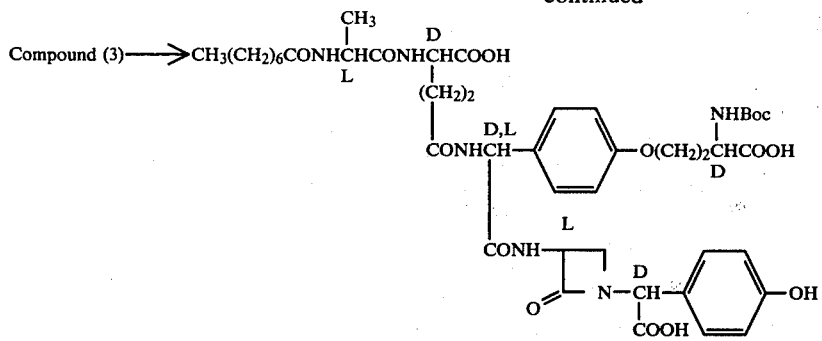

Octanoyl-L-Ala-γ-D-GLu(α-OH)(α)-Boc-(ω)-DL-Nocardicin C (4) was prepared substantially in the same manner as step 2 of Example 1.

IR (Nujol): 3300, 1730, 1650 cm$^{-1}$
NMR (CD$_3$OD), δ: 0.83 (3H, t, J=4 Hz), 1.16–1.33 (15H, m), 1.53 (9H, s), 2.10–2.31 (6H, m), 3.30 (1H, m), 3.91–4.4 (5H, m), 5.21 (1H, s), 5.36 (1H, s), 6.65–7.30 (8H, m).

(3) Step 3

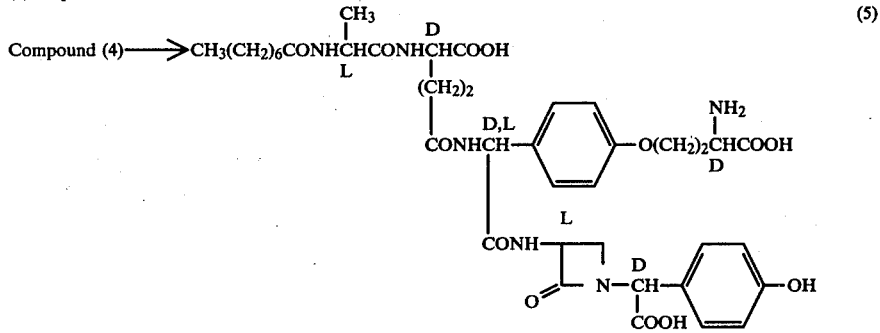

Octanoyl-L-Ala-γ-D-Glu(α-OH)-(α)-DL-Nocardicin C (5) was prepared substantially in the same manner as step 4 of Example 1.

IR (Nujol): 3250, 1735, 1640 cm$^{-1}$

NMR (DMSO-d$_6$), δ: 0.93 (3H, t, J=4 Hz), 1.13–1.30 (17H, m), 2.00–2.16 (1H, m), 3.50–3.66 (1H, m), 3.93–4.30 (5H, m), 5.23 (2H, broad s), 6.66–7.33 (8H, m)

EXAMPLE 10

(1) Step 1

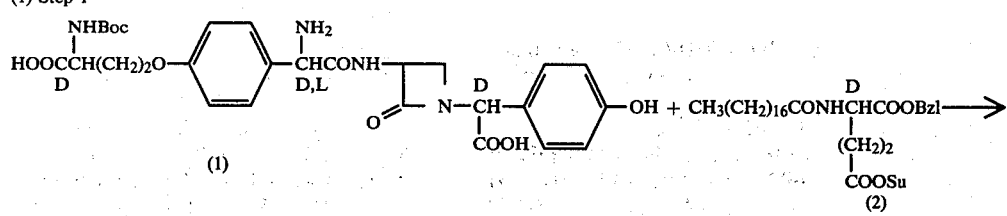

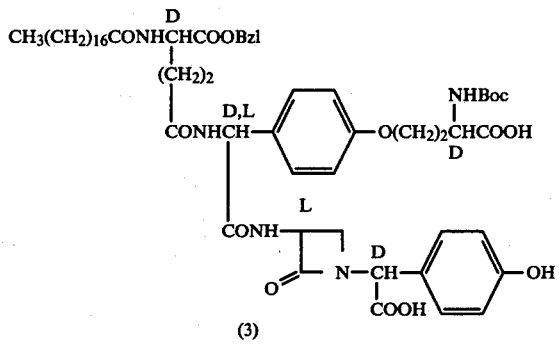

Stearoyl-D-Glu(α-OBzl)-OSu (2) (0.58 g) was added to a mixture of Boc-(ω)-DL-Nocardicin C (1) (0.57 g) and triethylamine (0.12 g) in a mixture of methylene chloride (20 ml) and methanol (4 ml).

The resulting mixture was stirred for 17 hours at room temperature and then evaporated. The residue was taken up in ethyl acetate (30 ml), washed with dilute hydrochloric acid and water, dried over magnesium sulfate and then evaporated to give a foamy residue. The residue was pulverized with ether to give stearoyl-γ-D-Glu(α-OBzl)-(α)-Boc-(ω)-D.L-Nocardicin C (3) (0.81 g).

IR (Nujol) cm$^{-1}$: 3300, 1735, 1650, 1610

NMR (CD$_3$OD), δ: 0.7–1.10 (3H, m), 1.10–1.80 (30H, m), 1.38 (9H, s), 180–2.10 (8H, m), 3.70–4.70 (5H, m), 5.12 (2H, s), 5.27 and 5.32 (1H, two s), 5.42 (1H, s), 6.70–7.40 (8H, m), 7.37 (5H, s)

(2) Step 2

Compound (3)⟶ (4)

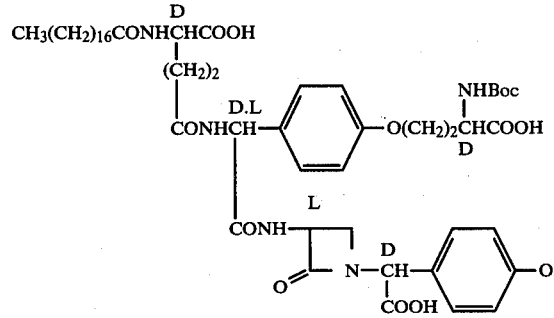

Stearoyl-γ-D-Glu(α-OBzl)-(α)-Boc-(ω)-D,L-Nocardicin C (3) (0.79 g) was dissolved in methanol (10 ml) and hydrogenated under 2.5 atmospheric pressure of hydrogen over 10% palladium charcoal (0.15 g). After removal of the catalyst, the solvent was evaporated under reduced pressure to give an oil, which was pulverized with ether to give stearoyl-γ-D-Glu(α-OH)-(α)-Boc-(ω)-DL-Nocardicin C (4) (0.63 g).

IR (Nujol) cm$^{-1}$: 3300, 1730, 1650, 1615

NMR (CD$_3$OD), δ: 0.70–1.10 (3H, m), 1.10–1.80 (30H, m), 1.80–2.70 (8H, m), 3.70–4.60 (5H, m), 5.30 (1H, s), 5.43 (1H, s), 6.70–7.40 (8H, m)

(3) Step 3

-continued

Compound (4)⟶ (5)

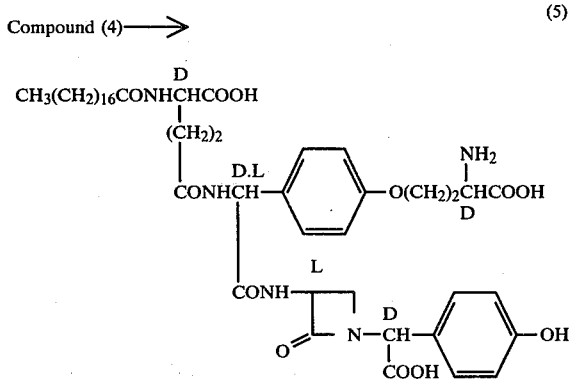

Stearoyl-γ-D-Glu(α-OH)-(α)-Boc-(ω)-DL-Nocardicin C (4) (0.61 g) was suspended in benzene (6 ml) and trifluoroacetic acid (6 ml) was added thereto. After stirring for 20 minutes at room temperature, the reaction mixture was poured into petroleum ether to give precipitates. The precipitates were subjected to column chromatography of HP-20 (20 ml) using 80% aqueous methanol as eluent. Fractions containing the object compound (5) were collected and evaporated under reduced pressure to give a foamy residue, which was pulverized with petroleum ether to give stearoyl-γ-D-Glu(α-OH)-(α)-DL-Nocardicin C (5) (0.23 g).

IR (Nujol) cm$^{-1}$: 3250, 1730, 1635, 1610

NMR (CD$_3$OD)+DMSOd$_6$) δ: 0.50–1.00 (3H, m), 1.00–2.70 (38H, m), 3.00 (1H, m), 3.40–3.90 (2H, m), 3.90–4.40 (3H, m), 5.22 (2H, s), 6.50–7.50 (8H, m)

EXAMPLE 11

(1) Step 1

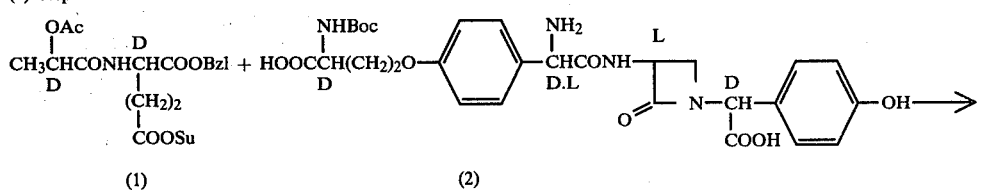

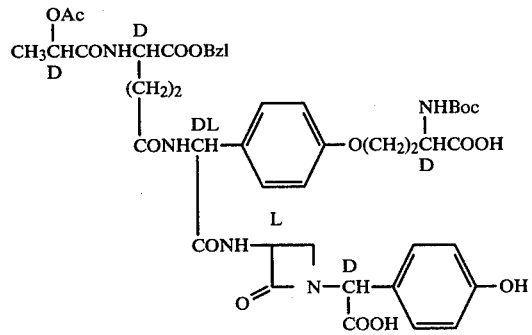

D-Lac(OAc)-γ-D-Glu(α-OBzl)-(α)-Boc-(ω)-D,L-Nocardicin C (3) was prepared substantially in the same manner as step 1 of Example 10.

(2) Step 2

Compound (3)⟶ (4)

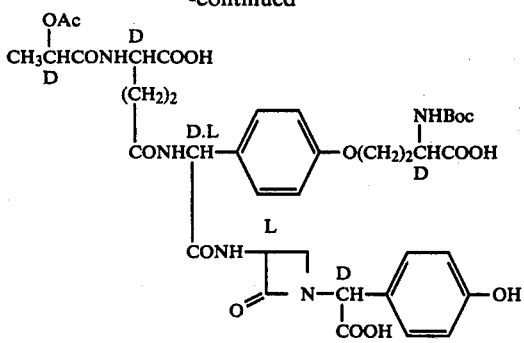

D-Lac(OAc)-γ-D-Glu(α-OH)-(α)-Boc-(ω)-DL-Nocardicin C (4) was prepared substantially in the same manner as step 2 of Example 10.

IR (Nujol) cm$^{-1}$: 3250, 1730, 1665

NMR (CD$_3$OD) δ: 1.42 (9H, s), 1.70–2.60 (6H, m), 2.07 (3H, s), 3.70–4.70 (6H, m), 5.30 (1H, s), 5.45 (1H, s), 6.70–7.50 (8H, m)

(3) Step 3

Compound (4) ⟶ (5)

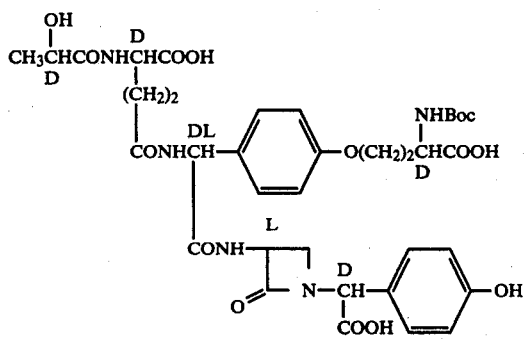

D-Lac(oAc)-γ-D-Glu(α-OH)-(α)-Boc-(ω)-DL-Nocardicin C (4) (0.72 g) was dissolved in a mixture of methanol (10 ml) and water (10 ml). The resulting mixture was adjusted to pH 10.5 with sodium carbonate and stirred at 0°–5° C. After a few minutes, the temperature was raised to 25° C, and the mixture was stirred for 6 hours. The reaction mixture was adjusted to pH 7.0 with diluted hydrochloric acid and concentrated. The resulting aqueous layer was adjusted to pH 2 with diluted hydrochloric acid and extracted with a mixture of methanol (20 ml) and ethyl acetate (180 ml). The organic layer was washed with water, dried over magnesium sulfate and evaporated to give an oil, which was pulverized with ether to give D-Lac-γ-D-Glu(α-OH)-(α)-Boc-(ω)-DL-Nocardicin C (5) (0.84 g).

IR (Nujol) cm$^{-1}$: 3250, 1710, 1640

NMR (CD$_3$OD) δ: 1.38 (9H, s), 1.70–2.50 (6H, m), 3.70–4.70 (6H, m), 5.30 (1H, s), 5.47 (1H, s), 6.70–7.50 (8H, m)

(4) Step 4

Compound (5) ⟶ (6)

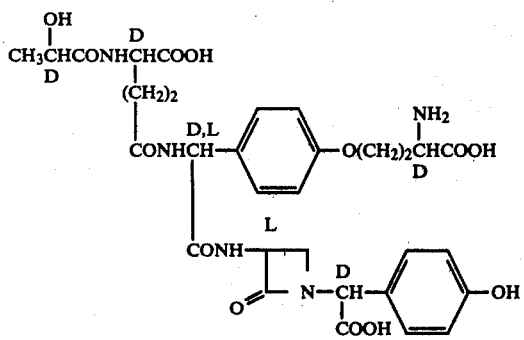

D-Lac-γ-D-Glu(α-OH)-(α)-DL-Nocardicin C (6) was prepared substantially in the same manner as step 3 of Example 10.

IR (Nujol) cm$^{-1}$: 3230, 1730, 1640, 1610

NMR (D$_2$O) δ: 1.73 (3H, two d, J=6 Hz), 1.70–2.60 (6H, m), 3.05 (1H, m), 3.73 (1H, m), 3.90–4.40 (5H, m), 5.24 (1H, s), 5.36 (1H, s), 6.60–7.40 (8H, m)

EXAMPLE 12

(1) Step 1

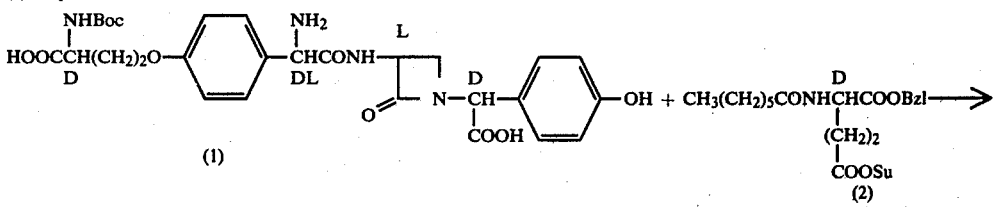

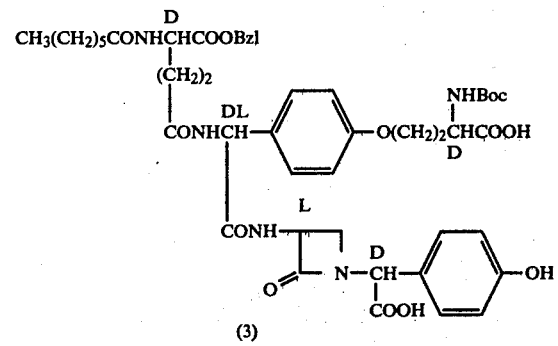

Heptanoyl-γ-D-Glu(α-OBzl)-(α)-Boc-(ω)-DL-Nocardicin C (3) (0.77 g) was prepared substantially in the same manner as step 1 of Example 10.

IR (Nujol) cm$^{-1}$: 3260, 1725, 1640

NMR (CD$_3$OD)δ: 0.67–1.67 (1H, m), 1.40 (9H, s), 1.80–2.50 (8H, m), 4.07 (2H, t, J=6 Hz), 4.30–4.50 (2H, m), 5.17 (2H, s), 5.27 (1H, s), 5.43 (1H, s), 6.70–7.50 (8H, m), 7.37 (5H, s)

(2) Step 2

Compound (3) ⟶ (4)

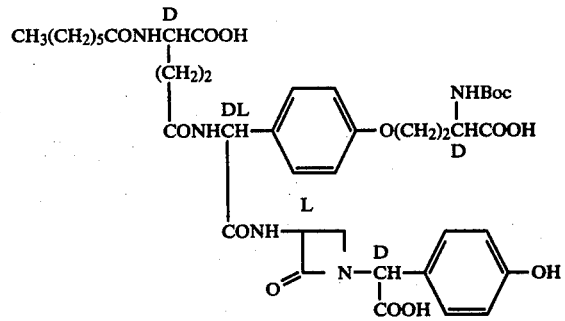

(1) Step 1

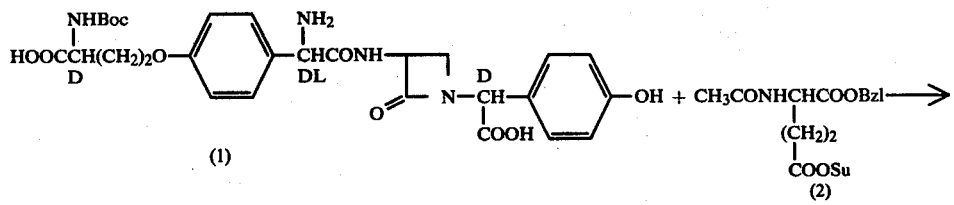

Heptanoyl-γ-D-Glu(α-OH)-(α)-Boc-(ω)-DL-Nocardicin C (4) was prepared substantially in the same manner as step 2 of Example 10.

IR (Nujol) cm$^{-1}$: 3250, 1710, 1640

NMR (CD$_3$OD)δ: 0.60–1.00 (3H, m), 1.00–1.80 (8H, m), 1.42 (9H, s), 1.80–2.50 (8H, m), 3.08 (1H, m), 3.76 (1H, m), 3.90–4.20 (2H, m), 4.20–4.50 (2H, m), 5.26 (1H, s), 5.40 (1H, s), 6.60–7.40 (8H, m)

(3) Step 3

Compound (4) ⟶ (5)

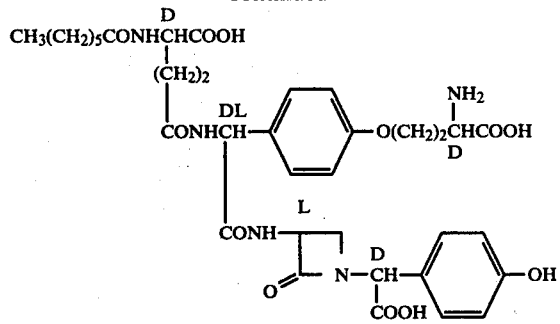

Heptanoyl-γ-D-Glu(α-OH)-(α)-DL-Nocardicin C (5) was prepared substantially in the same manner as step 3 of Example 10.

IR (Nujol) cm$^{-1}$: 3250, 1730, 1640

NMR (CD$_3$OD)δ: 0.70–1.00 (3H, m), 1.00–1.70 (8H, m) 1.70–2.70 (8H, m), 3.04 (1H, m), 3.78 (1H, m), 4.00–4.50 (4H, m), 5.26 (1H, s), 5.38 (1H, s), 6.60–7.40 (8H, m)

EXAMPLE 13

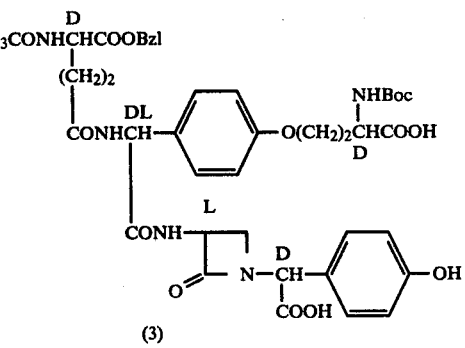

Acetyl-γ-D-Glu(α-OBzl)-(α)-Boc-(ω)-DL-Nocardicin C (3) was prepared substantially in the same manner as step 1 of Example 10.

IR (Nujol) cm$^{-1}$: 3280, 1730, 1650

NMR (CD$_3$OD)δ: 1.00–1.60 (12H, m), 1.60–2.50 (9H, m), 3.76 (1H, m), 3.90–4.10 (2H, m), 4.10–4.50 (2H, m), 5.12 (1H, s), 5.24 (1H, s), 5.38 (1H, s), 6.67–7.40 (8H, m), 7.31 (5H, s)

Compound (3) ⟶ (4)

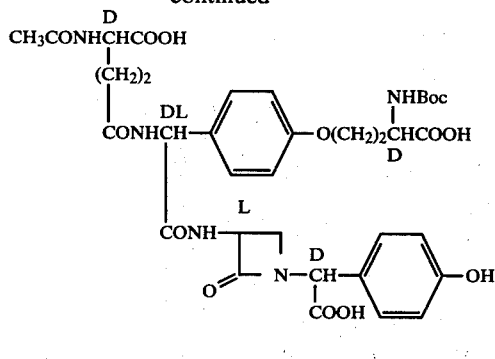

Acetyl-γ-D-Glu(α-OH)-(α)-Boc-(ω)-DL-Nocardicin C (4) was prepared substantially in the same manner as step 2 of Example 1.

IR (Nujol) cm$^{-1}$: 3300, 1730, 1650

NMR (CD$_3$OD)δ: 1.40 (9H, s), 1.90–2.60 (9H, m), 3.70–4.60 (5H, m), 5.30 (1H, s), 5.43 (1H, s), 6.70–7.50 (8H, m)

Acetyl-γ-D-Glu(α-OH)-(α)-DL-Nocardicin C (5) was prepared substantially in the same manner as step 3 of Example 1.

IR (Nujol) cm$^{-1}$: 3250, 1730, 1640

NMR (D$_2$O)δ: 1.96 and 1.98 (3H, two s), 2.00–2.60 (6H, m), 3.05 (1H, m), 3.72 (1H, m), 3.90–4.40 (4H, m), 5.27 (1H, s), 5.34 (1H, s), 6.70–7.40 (8H, m)

EXAMPLE 14

(1) Step 1

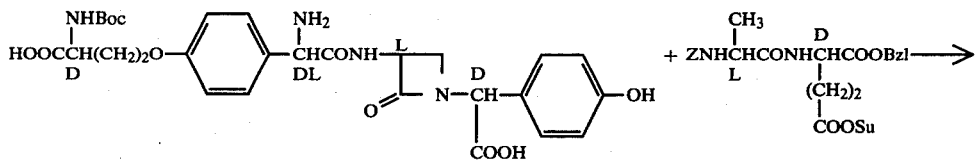

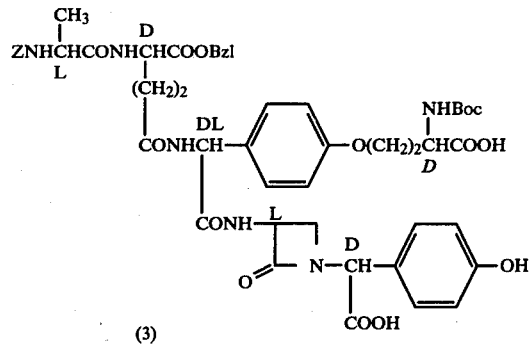

(3) Step 3

Compound (4) ⟶

Z-L-Ala-γ-D-Glu(α-OBzl)-(α)-Boc-(ω)-DL-Nocardicin C (3) was prepared substantially in the same manner as step 1 of Example 1.

IR (Nujol) cm$^{-1}$: 3250, 1730, 1650, 1610

NMR (CD₃OD)δ: 1.40 (9H, s), 1.70–2.50 (6H, m), 3.70–4.50 (6H, m), 5.05 (2H, s), 5.13 (2H, s), 5.27 and 5.33 (1H, two s), 6.70–7.50 (8H, m), 7.28 (10H, s)

(2) Step 2

Compound (3) ⟶

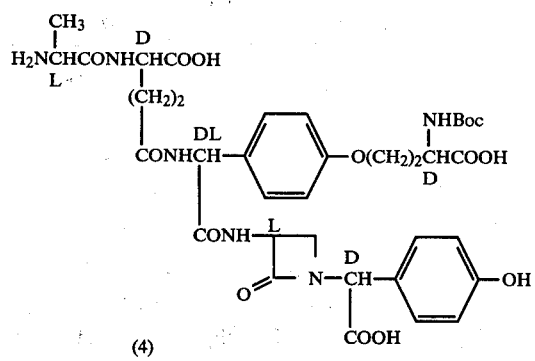

(4)

L-Ala-γ-D-Glu(α-OH)-(α)-Boc-(ω)-DL-Nocardicin C (4) was prepared substantially in the same manner as step 2 of Example 1.

IR (Nujol) cm⁻¹: 3280, 1730, 1680, 1610

NMR (CD₃OD): 1.43 (9H, s), 1.90–2.60 (6H, m), 3.07 (1H, m), 3.70–4.60 (6H, m), 5.32 (2H, s), 6.70–7.50 (8H, m)

(3) Step 3

Compound (4) ⟶

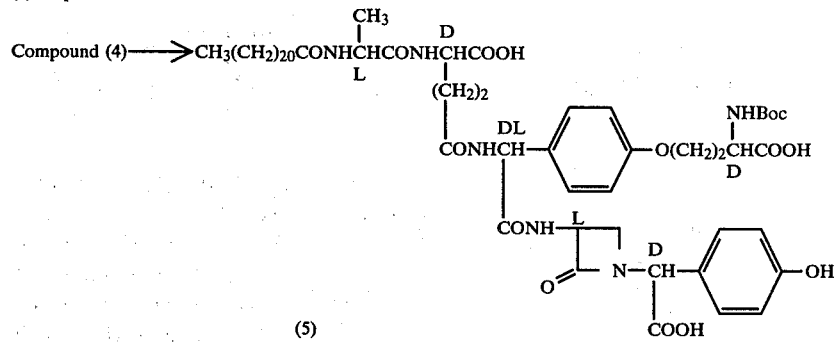

(5)

Behenoyl-L-Ala-γ-D-Glu(α-OH)-(α)-Boc-(ω)-DL-Nocardicin C (5) was prepared substantially in the same manner as step 1 of Example 6.

NMR (CDCl₃-CD₃OD)δ: 0.70–1.10 (3H, m), 1.10–1.80 (38H, m), 1.43 (9H, s), 1.80–2.60 (8H, m), 3.70–4.40 (6H, m), 4.93 (1H, m), 5.33 (1H, s), 5.47 (1H, s), 6.70–7.50 (8H, m)

(4) Step 4

Compound (5) ⟶

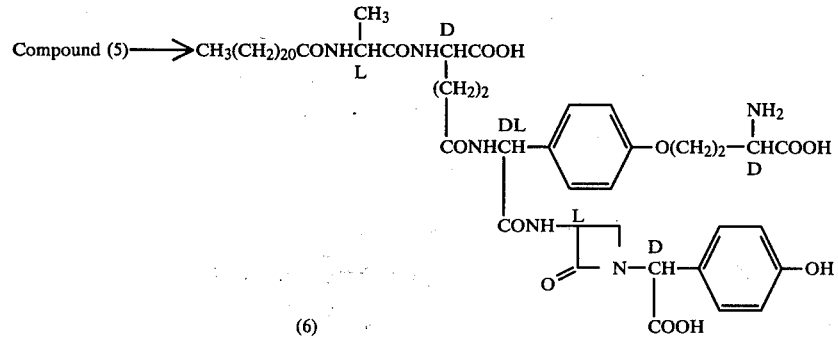

(6)

Behenoyl-L-Ala-γ-D-Glu(α-OH)-(α)-DL-Nocardicin C (6) was prepared substantially in the same manner as step 3 of Example 1.

IR (Nujol) cm⁻¹: 3260, 1735, 1640

NMR (CD₃OD-DMSOd₆)δ: 0.60–1.00 (3H, m), 1.00–1.70 (38H, m), 1.70–2.40 (8H, m), 3.50–3.90 (2H, m), 4.86 (1H, m), 5.32 (2H, s), 6.60–7.40 (8H, m)

EXAMPLE 15

(1) Step 1

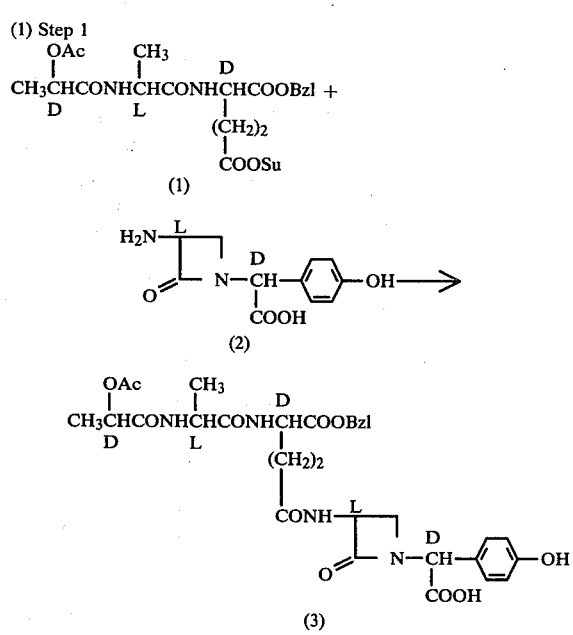

D-Lac(OAc)-L-Ala-γ-D-Glu(α-OBzl)OSu (1) (610 mg) was added to a mixture of 3-ANA (2) (280 mg) and sodium bicarbonate (120 mg) in acetone (5 ml) and water (10 ml). The mixture was stirred for 17 hours at room temperature. The solvent was evaporated under reduced pressure and the residue was dissolved in ethyl acetate, washed with dilute hydrochloric acid and water, dried over magnesium sulfate and then evaporated to give an oil. The oil was pulverized with ether to give D-Lac(OAc)-L-Ala-γ-D-Glu(α-OBzl)-3ANA (3) (590 mg).

I.R. (Nujol): 3250 (broad), 1730, 1650 cm$^{-1}$

N.M.R. (CD$_3$OD),δ: 1.32 (d, 3H, J=7 Hz), 1.38 (d, 3H, J=7 Hz), 1.90-2.50 (m, 4H), 2.00 (s, 3H), 3.02 (m, 1H), 3.75 (m, 1H), 4.10-4.70 (m, 3H), 5.08 (s, 2H), 5.38 (s, 1H), 5.95 (ABq, 4H, J=8 Hz), 7.27 (s, 5H)

(2) Step 2

Compound (3)⟶

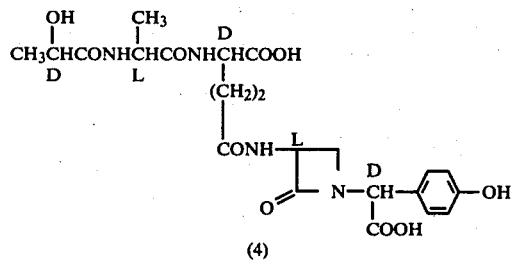

(4)

p D-Lac(OAc)-L-Ala-γ-D-Glu(α-OBzl)-3ANA (3) (450 mg) was dissolved in 1 N sodium hydroxide (3.5 ml) and the solution was stirred for 30 minutes at room temperature. The reaction mixture was adjusted to pH 2 with dilute hydrochloric acid and extracted with ethyl acetate (30 ml). The aqueous layer was evaporated under reduced pressure and the residue was subjected to column chromatography using HP-20 (20 ml) with aqueous methanol as an eluent. The fractions containing the object Compound (4) were collected and evaporated under reduced pressure. The residue was dissolved in water and lyophilized to give D-Lac-L-Ala-γ-D-Glu(α-OH)-3ANA (4) (150 mg).

I.R. (Nujol): 3300, 1730, 1650, 1530, 1515 cm$^{-1}$

N.M.R. (D$_2$O),δ: 1.36 (d, 3H, J=7 Hz), 1.40 (d, 3H, J=7 Hz), 1.6-2.6 (m, 4H), 3.10 (m, 1H), 3.75 (m, 1H), 4.00-4.40 (m, 3H), 5.40 (s, 1H), 7.06 (ABq, 4H, J=8 Hz)

EXAMPLE 16

(1) Step 1

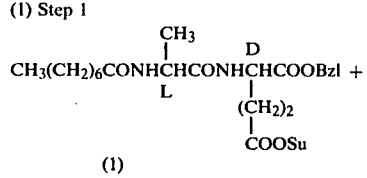

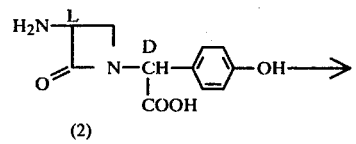

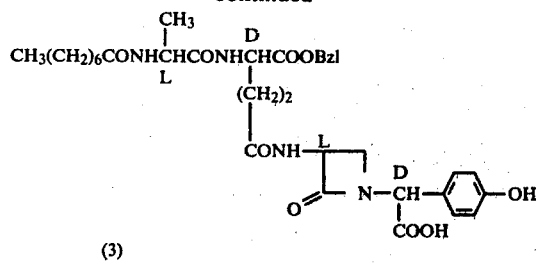

(3)

Octanoyl-L-Ala-γ-D-Glu(α-OBzl)-3ANA (3) was prepared substantially in the same manner as step 1 of Example 15.

I.R. (Nujol): 3250, 1740, 1645 cm$^{-1}$

N.M.R. (CD$_3$OD),δ: 0.70-2.40 (m, 22H), 2.95 (m, 1H), 3.73 (m, 1H), 3.90-4.50 (m, 2H), 4.90 (m, 1H), 5.10 (s, 2H), 5.32 (s, 1H), 6.95 (ABq, 4H, J=8 Hz), 7.30 (s, 5H)

(2) Step 2

Compound (3)⟶

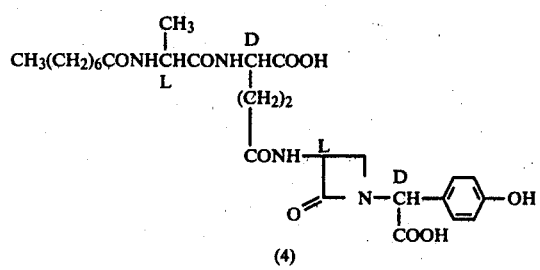

(4)

Octanoyl-L-Ala-γ-D-Glu(α-OBzl)-3ANA (3) (350 mg) was dissolved in methanol (10 ml) and hydrogenated under 2.5 atomospheric pressure of hydrogen over 10% palladium charcoal (70 mg). After removal of the catalyst, the solvent was evaporated under reduced pressure to give an oil. The oil was pulverized with ether to give octanoyl-L-Ala-γ-D-Glu(α-OH)-3ANA (4) (250 mg).

I.R. (Nujol): 3290, 1735, 1640 cm$^{-1}$

N.M.R. (CD$_3$OD)δ: 0.70-1.00 (m, 3H), 1.00-2.40 (m, 19H), 3.06 (m, 1H), 3.82 (m, 1H), 4.10-4.50 (m, 2H), 5.45 (s, 1H), 7.00 (ABq, 4H, J=7 Hz)

EXAMPLE 17

(1) Step 1

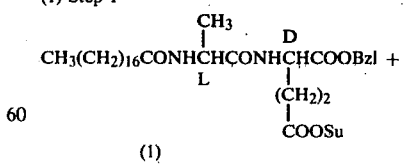

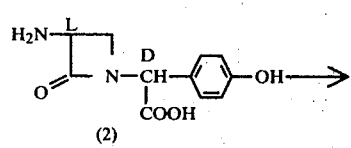

-continued

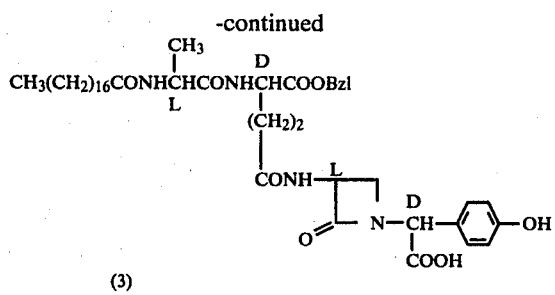
(3)

(1) Step 1

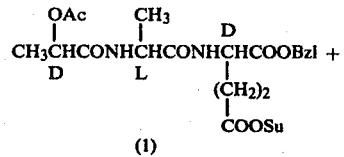
(1)

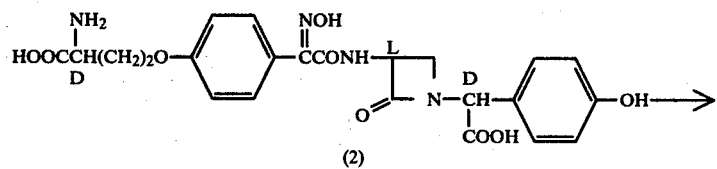
(2)

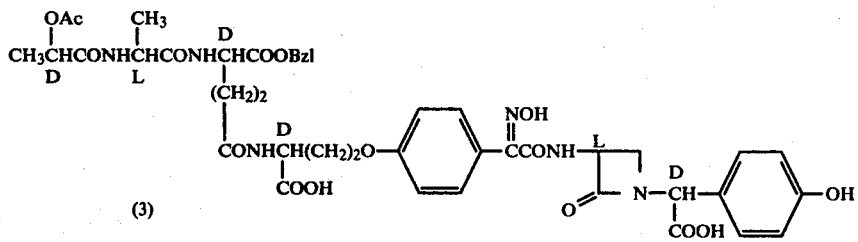
(3)

Stearoyl-L-Ala-γ-D-Glu(α-OBzl)-3ANA (3) was prepared substantially in the same manner as step 1 of Example 15.

I.R. (Nujol): 3260, 1725, 1630 cm$^{-1}$
N.M.R. (CDCl$_3$-CD$_3$OD)δ: 0.7–1.10 (m, 3H), 1.10–1.70 (m, 36H), 2.00–2.60 (m, 6H), 4.97 (m, 1H), 5.18 (ABq, 2H, J=6 Hz), 5.50 (s, 1H), 7.05 (ABq, 4H, J=8 Hz), 7.03 (s, 5H)

(2) Step 2

Compound (3) ⟶

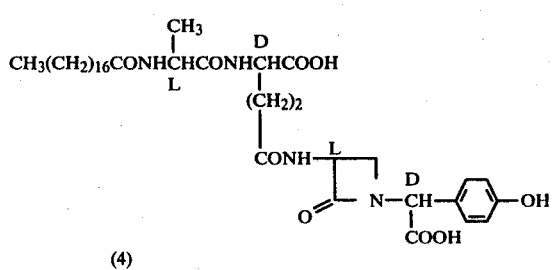
(4)

(2) Step 2

Compound (3) ⟶

Stearoyl-L-Ala-γ-D-Glu(α-OH)-3ANA (4) was prepared substantially in the same manner as step 2 of Example 16.

I.R. (Nujol): 3290, 1730, 1640 cm$^{-1}$
N.M.R. (CDCl$_3$-CD$_3$OD)δ: 0.70–1.10 (m, 3H), 1.10–1.80 (m, 36H), 2.00–2.70 (m, 6H), 3.15 (m, 1H), 3.60–4.10 (m, 3H), 4.97 (m, 1H), 5.47 (s, 1H), 6.98 (ABq, 4H, J=8 Hz)

EXAMPLE 18

D-Lac(OAc)-L-Ala-γ-D-Glu(α-OBzl)OSu (1) (570 mg) was added to a mixture of Nocardicin A (2) (500 mg) and triethylamine (210 mg) in acetone (20 ml) and water (10 ml). The resulting mixture was stirred for 17 hours at room temperature and the solvent was evaporated in vacuo. The residue was taken up in ethyl acetate (50 ml), washed with dilute hydrochloric acid and water, dried over magnesium sulfate and then evaporated to give D-Lac(OAc)-L-Ala-γ-D-Glu-(α-OBzl)-Nocardicin A (3) (870 mg).

I.R. (Nujol): 3280, 1735, 1650 cm$^{-1}$
N.M.R. (CD$_3$OD)δ: 1.31 (d, 3H, J=6 Hz), 1.38 (d, 3H, J=6 Hz), 2.05 (s, 3H), 2.00–2.26 (m, 4H), 3.85–4.66 (m, 6H), 5.11 (s, 2H), 5.45 (s, 1H), 6.66–7.55 (m, 8H), 7.26 (s, 5H)

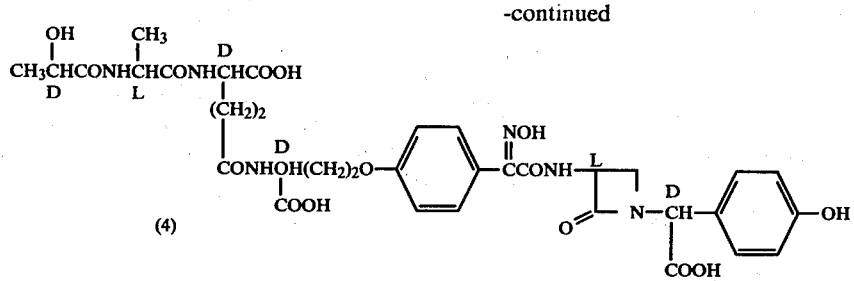

(4)

D-Lac(OAc)-L-Ala-γ-D-Glu(α-OBzl)-Nocardicin A (3) (570 mg) was dissolved in 0.5 N sodium hydroxide (8 ml) and the solution was stirred for 5 hours at room temperature. The reaction mixture was adjusted to pH 2 with dilute hydrochloric acid and extracted with ethyl acetate (30 ml). The organic layer was washed with water, dried over magnesium sulfate and evaporated to give a foamy residue. The residue was pulverized with ether to give D-Lac-L-Ala-γ-D-Glu(α-OH)-Nocardicin A (4) (220 mg).

I.R. (Nujol): 3250, 1725, 1660–1640 cm$^{-1}$
N.M.R. (CD$_3$OD)δ: 1.38 (d, 6H, J=6 Hz), 2.16–2.43 (m, 4H), 3.80–4.66 (m, 6H), 5.50 (s, 1H), 6.81 (d, 2H, J=7 Hz), 6.95 (d, 2H, J=7 Hz), 7.21 (d, 2H, J=7 Hz), 7.51 (d, 2H, J=7 Hz)

D-Lac(OAc)-L-Ala-γ-D-Glu(α-OBzl)-Nocardicin A (2) (870 mg) was dissolved in methanol (30 ml) and hydrogenated under 2.5 atomospheric pressure of hydrogen over palladium-charcoal (200 mg). After removal of the catalyst, the solvent was concentrated under reduced pressure. The residue was pulverized with acetone to give D-Lac(OAc)-L-Ala-γ-D-Glu(α-OH)-D,L Nocardicin C (2) (650 mg).

I.R. (Nujol): 3250, 1730, 1650 cm$^{-1}$
N.M.R. (D$_2$O)δ: 1.41–1.63 (m, 6H), 1.91–2.50 (m, 6H), 2.23 (s, 3H), 3.00–3.16 (m, 1H), 3.70–4.50 (m, 7H), 5.20 (s, 1H), 5.45 (s, 1H), 6.91–7.58 (m, 8H)

(2) Step 2

Compound (2) ⟶

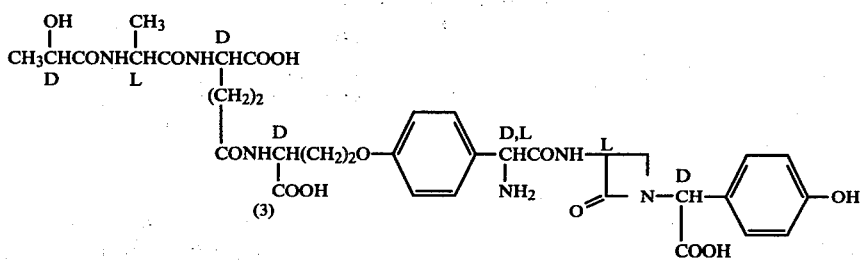

(3)

D-Lac-L-Ala-γ-D-Glu(α-OH)-D,L Nocardicin C (3) was prepared substantially in the same manner as Step 2 of Example 18.

I.R. (Nujol): 3250, 1735, 1660–1640 cm$^{-1}$

EXAMPLE 19

(1) Step 1

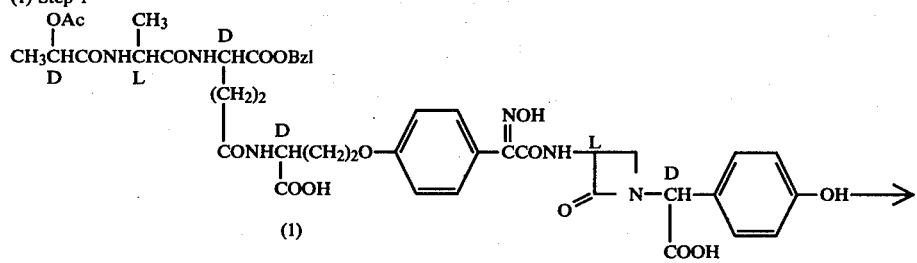

(1)

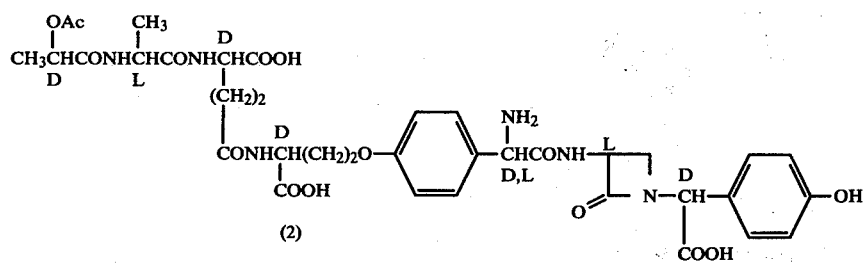

(2)

N.M.R. (D₂O)δ: 1.41 (d, 3H, J=7 Hz), 1.45 (d, 3H, J=7 Hz), 1.91–2.46 (m, 6H), 3.00–3.16 (m, 1H), 3.70–4.66 (m, 7H), 5.16 (s, 1H), 5.43 (s, 1H), 6.91 (d, 2H, J=6 Hz), 7.08 (d, 2H, J=6 Hz), 7.25 (d, 2H, J=6 Hz), 7.41 (d, 2H, J=6 Hz)

PREPARATION 4

(1) Step 1

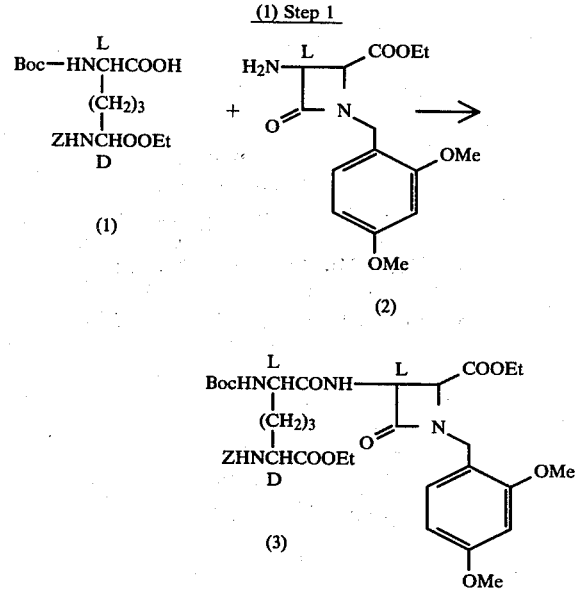

3-{Boc(L)-Z-(D)-mesoDAP-(D)-OEt-(L)}amino-1-(2',4'-dimethoxy)benzyl-4-ethoxycarbonylazetidin-2-one (3) was prepared substantially in the same manner as that of Preparation 1.

IR (Nujol): 3260, 1760, 1730, 1685, 1660, 1610 cm⁻¹

NMR (CD₃OD, δ): 1.0–2.0 (12H, m), 1.47 (9H, s), 3.85 (6H, s), 4.0–4.6 (9H, m), 5.15 (2H, s), 6.4–6.7 (2H, m), 7.18 (1H, d, J=9 Hz), 7.40 (5H, s)

(2) Step 2

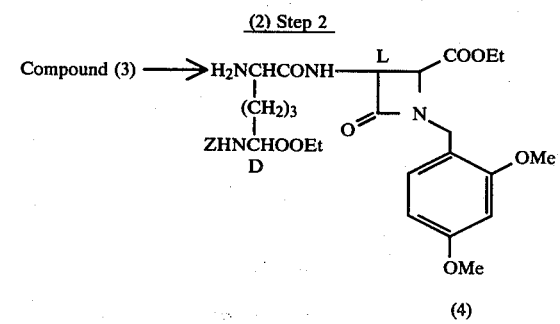

3-{Z-(D)-mesoDAP-(D)-OEt-(L)}amino-1-(2',4'-dimethoxy)benzyl-4-ethoxycarbonylazetidin-2-one (4) was prepared substantially in the same manner as that of preparation 3.

IR (Nujol): 3230 (broad), 1730, 1680 cm⁻¹

NMR (CD₃OD, δ): 1.27 (6H, t, J=7 Hz), 1.4–2.0 (6H, m), 3.85 (6H, s), 4.0–4.6 (9H, m), 5.13 (2H, s), 6.4–6.7 (2H, m), 7.18 (1H, d, J=9 Hz), 7.38 (5H, s)

PREPARATION 5

(1) Step 1

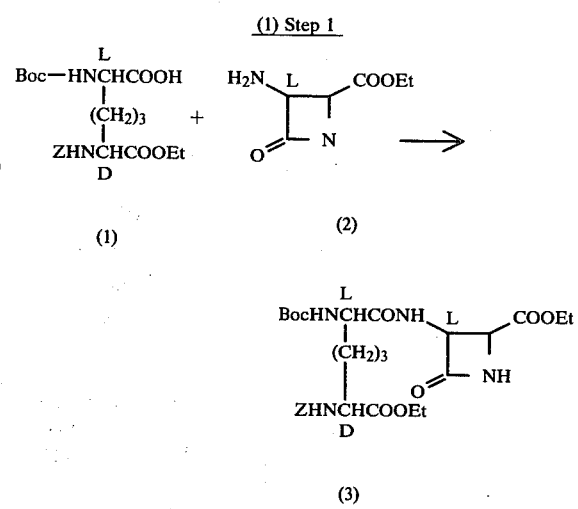

3-{Boc-(L)-Z-(D)mesoDAP(D)-OEt-(L)}amino-4-ethoxycarbonylazetidin-2-one (3) was prepared in substantially the same manner as that of Preparation 1.

IR (film): 3260, 1760, 1700 (broad) cm⁻¹

NMR (CD₃OD, δ): 1.23 (6H, t, J=7 Hz), 1.43 (9H, s), 1.1–2.0 (6H, m), 3.8–4.6 (7H, m), 5.10 (2H, s), 7.35 (5H, s)

(2) Step 2

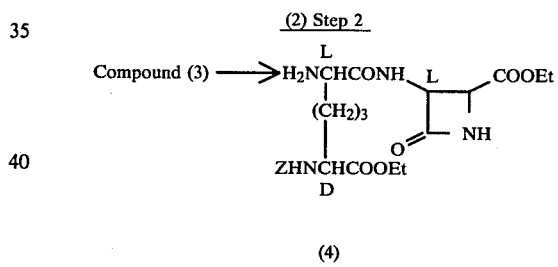

3-{Z-(D)mesoDAP(D)-OEt-(L)}amino-4-ethoxycarbonylazetidin-2-one (4) was prepared in substantially the same manner that of Preparation 3.

IR (Nujol): 3230 (broad), 1710 (broad), 1670 cm⁻¹

NMR (CD₃OD, δ): 1.25 (3H, t, J=7 Hz), 1.28 (3H, t, J=7 Hz), 1.5–2.2 (6H, m), 3.7–4.6 (7H, m), 5.13 (2H, s), 7.37 (5H, s)

EXAMPLE 20

(1) Step 1

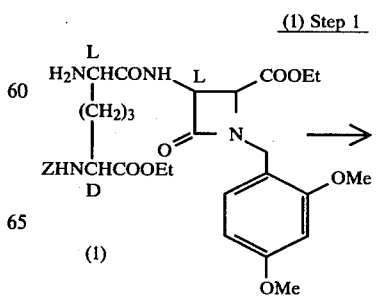

-continued
(1) Step 1

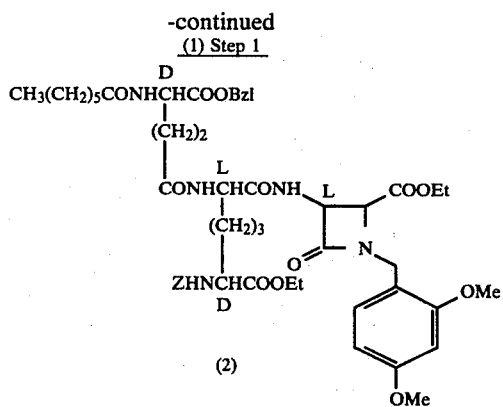

3-{heptanoyl-γ-D-Glu(α-OBzl)-(L)-Z-(D)-mesoDAP-(D)-OEt-(L)}amino-1-(2',4'-dimethoxy)benzyl-4-ethoxycarbonylazetidin-2-one (2) was prepared substantially in the same manner as that of step (1) of Example 6.

IR (Nujol): 3250, 1730, 1680, 1635 cm$^{-1}$

NMR (CD$_3$OD-CDCl$_3$, δ): 0.7–1.0 (3H, m), 1.0–2.0 (20H, m), 2.0–2.4 (6H, m), 3.77 (3H, s), 3.79 (3H, s), 4.0–4.6 (9H, m), 5.08 (2H, s), 5.15 (2H, s), 6.4–6.6 (2H, m), 7.10 (1H, d, J=9 Hz), 7.34 (10H, s)

(2) Step 2

Compound (2) ⟶

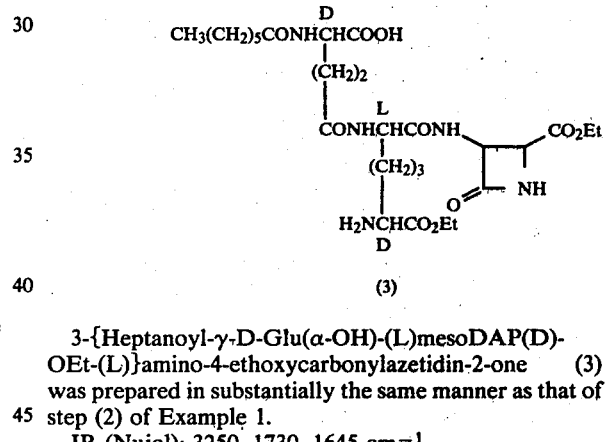

3{heptanoyl-γ-D-glu(α-OH)-(L)-mesoDAP-(D)-OEt-(L)}amino-1-(2',4'-dimethoxy)benzyl-4-ethoxycarbonylazetidin-2-one (3) was prepared substantially in the same manner as that of step (2) of Example 1.

IR (Nujol): 3240, 1735, 1630, 1600 cm$^{-1}$

NMR (CD$_3$OD, δ): 0.8–1.0 (3H, m), 1.0–2.4 (26H, m), 3.76 (6H, s), 3.8–4.6 (9H, m), 5.21 (1H, m), 6.3–6.6 (2H, m), 7.09 (1H, d, J=9 Hz)

EXAMPLE 21

(1) Step 1

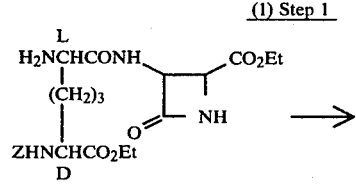

(1) ⟶

-continued
(1) Step 1

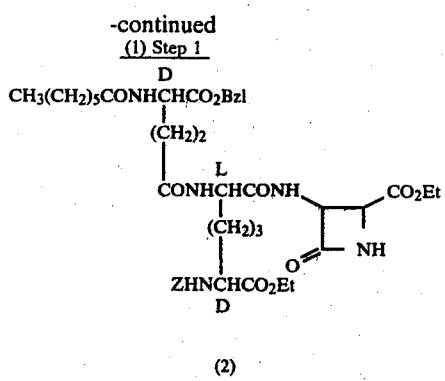

3-{Heptanoyl-γ-D-Glu(α-OBzl)-Z-(D)mesoDAP(D)-OEt-(L)}amino-4-ethoxycarbonylazetidin-2-one (2) was prepared in substantially the same manner as that of step (1) of Example 1.

IR (Nujol): 3260, 1770, 1730, 1685, 1640 cm$^{-1}$

NMR (CDCl$_3$-CD$_3$OD, δ): 0.70–2.50 (29H, m), 3.80–4.70 (8H, m), 5.10 (2H, s), 5.17 (2H, s), 7.35 (10H, s)

(2) Step 2

Compound (2) ⟶

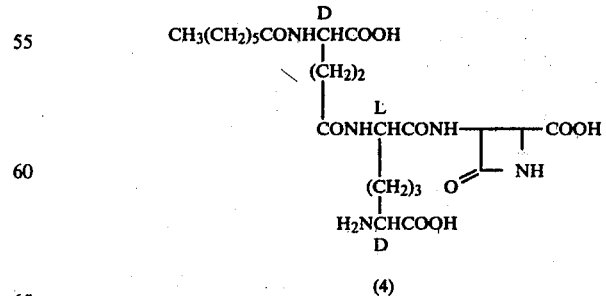

3-{Heptanoyl-γ-D-Glu(α-OH)-(L)mesoDAP(D)-OEt-(L)}amino-4-ethoxycarbonylazetidin-2-one (3) was prepared in substantially the same manner as that of step (2) of Example 1.

IR (Nujol): 3250, 1730, 1645 cm$^{-1}$

NMR (CD$_3$OD, δ): 0.70–2.50 (29H, m), 3.80–4.50 (8H, m)

(3) Step 3

Compound (3) ⟶

[structure (4)]

(4)

3-{Heptanoyl-γ-D-Glu(α-OH)-(L)-mesoDAP(D)-OEt-(L)}amino-4-ethoxycarbonylazetidin-2-one (3) (210 mg) was suspended in water (5 ml) and 1 N sodium hydroxide was added thereto. After stirring for 30 minutes at 0° C., the reaction mixture was adjusted to pH 2 with dilute hydrochloric acid and subjected to column chromatography using HP-20 (5 ml) eluting with 50% aqueous methanol. The fractions containing the object compound were collected and evaporated under reduced pressure to give a foamy residue, which was pulverized with ether to give 3-{heptanoyl-γ-D-Glu(α-OH)-(L)-mesoDAP(L)}amino-4-methoxycarbonylazetidin-2-one (4) (130 mg).

IR (Nujol): 3250, 1740 (broad); 1640 (broad) cm$^{-1}$
NMR (D$_2$O, δ): 0.6–1.00 (3H, m), 1.00–2.60 (20H, m), 3.68 (1H, m), 4.00–4.40 (3H, m), 5.18 (1H, m)

We claim:
1. A compound of the following formula or its pharmaceutically acceptable salt:

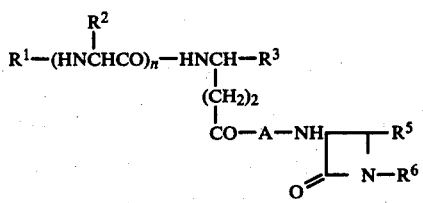

wherein
R$^1$ is hydrogen or acyl;
wherein the acyl may be substituted by a member of the group consisting of amino, halogen, hydroxy, protected hydroxy or carboxy;
R$^2$ is lower alkyl;
R$^3$ is carboxy or protected carboxy;
A is a bond, a group of the formula:

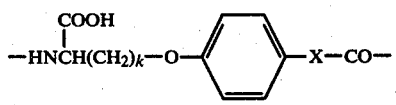

wherein X is a group of the formula:

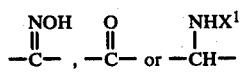

wherein X$^1$ is hydrogen or an amino protective group, and k is an integer of 1 to 4; or a group of the formula:

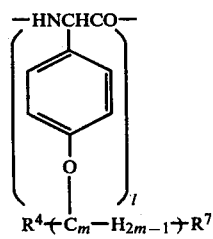

wherein R$^4$ is amino or protected amino,
R$^7$ is carboxy or protected carboxy,
m is an integer of 1 to 8, and l is an integer of 1 or 0;
R$^5$ is hydrogen, carboxy or esterified carboxy;
R$^6$ is hydrogen, ar(lower)alkyl wherein the alkyl moiety may have carboxy or protected carboxy and the aryl moiety may have one or more substituents selected from hydroxy, protected hydroxy and lower alkoxy; and
n is an integer of 1 or 0.

2. A compound according to claim 1, wherein R$^1$ is hydrogen, alkanoyl which may have hydroxy, ar(lower)alkanoyl, and R$^2$, R$^3$, R$^5$, R$^6$, n and A are each as defined in claim 1.

3. A compound according to claim 2, wherein R$^1$ is a group selected from hydrogen, acetyl, propionyl, 2-hydroxypropionyl, 2-acetoxypropionyl, heptanoyl, octanoyl, stearoyl, behenoyl, phenylacetyl and benzyloxycarbonyl, and R$^2$, R$^3$, R$^5$, R$^6$, n and A are each as defined in claim 1.

4. A compound according to claim 2 or 3, wherein A is bond.

5. A compound according to claim 2 or 3, wherein A is a group of the formula:

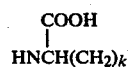

wherein k is as defined in claim 1.

6. A compound according to claim 2 or 3, wherein A is a group of the formula:

wherein k is as defined in claim 1.

7. A compound according to claim 2 or 3, wherein A is a group of the formula:

wherein k and X$^1$ are each as defined in claim 1.

8. A compound according to claim 2 or 3, wherein A is a group of the formula:

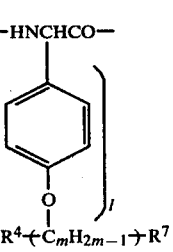

wherein l, m, R$^4$ and R$^7$ are each as defined in claim 1.

9. A compound according to claim 1 wherein:
R$^1$ is 2-acetoxyproprionyl, n is an integer 1,
R$^2$ is methyl,
R$^3$ is benzyloxycarbonyl,
A is a group of the formula:

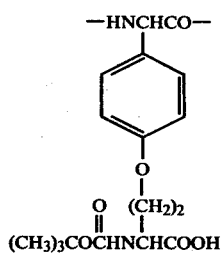

$R^5$ is hydrogen and
$R^6$ is α-carboxy-4-hydroxybenzyl.

10. A compound according to claim 1, wherein
$R^1$ is 2-acetoxypropionyl, n is an integer of 1,
$R^2$ is methyl, $R^3$ is carboxy, A is a group of the formula:

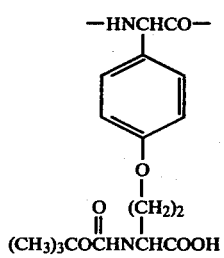

$R^5$ is hydrogen and $R^6$ is α-carboxy-4-hydroxybenzyl.

11. A compound according to claim 1 wherein
$R^1$ is 2-hydroxypropionyl, n is an integer of 1,
$R^2$ is methyl, $R^3$ is carboxy, A is a group of the formula:

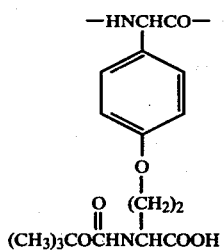

$R^5$ is hydrogen and $R^6$ is a α-carboxy-4-hydroxybenzyl.

12. A compound according to claim 1, wherein
$R^1$ is 2-hydroxypropionyl, n is an integer of 1,
$R^2$ is methyl, $R^3$ is carboxy, A is a group of the formula:

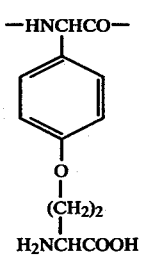

$R^5$ is hydrogen and $R^6$ is α-carboxy-4-hydroxybenzyl.

13. A compound according to claim 1, wherein
$R^1$ is 2-acetoxypropionyl, n is an integer of 1,
$R^2$ is methyl, $R^3$ is benzyloxycarbonyl, A is a group of the formula:

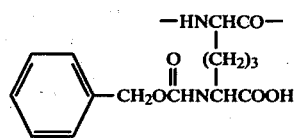

$R^5$ is hydrogen and $R^6$ is α-carboxy-4-hydroxybenzyl.

14. A compound according to claim 1, wherein
$R^1$ is 2-acetoxypropionyl, n is an integer of 1,
$R^2$ is methyl, $R^3$ is carboxy, A is a group of the formula:

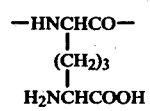

$R^5$ is hydrogen and $R^6$ is α-carboxy-4-hydroxybenzyl.

15. A compound according to claim 1, wherein
$R^1$ is 2-hydroxypropionyl, n is an integer of 1,
$R^2$ is methyl, $R^3$ is carboxy, A is a group of the formula:

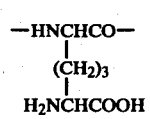

$R^5$ is hydrogen and $R^6$ is α-carboxy-4-hydroxybenzyl.

16. A compound according to claim 1, wherein
$R^1$ is octanoyl, n is an integer of 1,
$R^2$ is methyl, $R^3$ is benzyloxycarbonyl, A is a group of the formula:

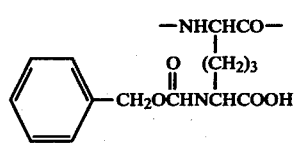

$R^5$ is hydrogen and $R^6$ is α-carboxy-4-hydroxybenzyl.

17. A compound according to claim 1, wherein
$R^1$ is octanoyl, n is an integer of 1,
$R^2$ is methyl, $R^3$ is carboxy, A is the group of the formula:

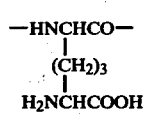

$R^5$ is hydrogen and $R^6$ is α-carboxy-4-hydroxybenzyl.

18. A compound according to claim 1, wherein
$R^1$ is stearoyl, n is an integer of 1,
$R^2$ is methyl, $R^3$ is benzyloxycarbonyl, A is a group of the formula:

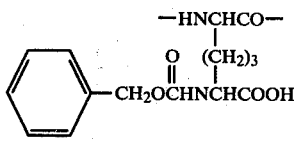

$R^5$ is hydrogen and $R^6$ is α-carboxy-4-hydroxybenzyl.

19. A compound according to claim 1, wherein
$R^1$ is stearoyl, n is an integer of 1,
$R^2$ is methyl, $R^3$ is carboxy, A is a group of the formula:

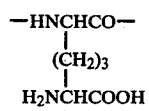

$R^5$ is hydrogen and $R^6$ is α-carboxy-4-hydroxybenzyl.

20. A compound according to claim 1, wherein
$R^1$ is benzyloxycarbonyl, n is an integer of 1,
$R^2$ is methyl, $R^3$ is carboxy, A is a group of the formula:

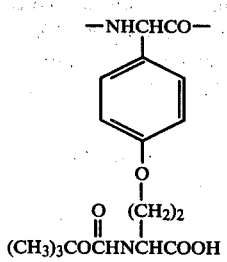

$R^5$ is hydrogen and $R^6$ is α-carboxy-4-hydroxybenzyl.

21. A compound according to claim 1, wherein
$R^1$ is hydrogen, n is an integer of 1,
$R^2$ is methyl, $R^3$ is carboxy, A is a group of the formula:

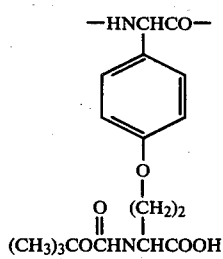

$R^5$ is hydrogen and $R^6$ is α-carboxy-4-hydroxybenzyl.

22. A compound according to claim 1, wherein
$R^1$ is hydrogen, n is an integer of 1,
$R^2$ is methyl, $R^3$ is carboxy, A is a group of the formula:

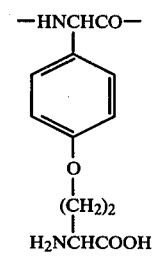

$R^5$ is hydrogen and $R^6$ is α-carboxy-4-hydroxybenzyl.

23. A compound according to claim 1, wherein
$R^1$ is phenylacetyl, n is an integer of 1,
$R^2$ is methyl, $R^3$ is carboxy, A is a group of the formula:

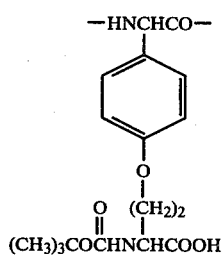

$R^5$ is hydrogen and $R^6$ is α-carboxy-4-hydroxybenzyl.

24. A compound according to claim 1, wherein
$R^1$ is phenylacetyl, n is an integer of 1,
$R^2$ is methyl, $R^3$ is carboxy, A is a group of the formula:

$R^5$ is hydrogen and $R^6$ is α-carboxy-4-hydroxybenzyl.

25. A compound according to claim 1, wherein
$R^1$ is stearoyl, n is an integer of 1,
$R^2$ is methyl, $R^3$ is carboxy, A is a group of the formula:

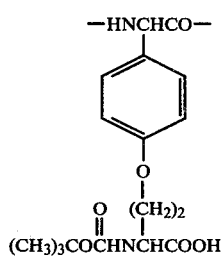

$R^5$ is hydrogen and $R^6$ is α-carboxy-4-hydroxybenzyl.

26. A compound according to claim 1, wherein
$R^1$ is stearoyl, n is an integer of 1,
$R^2$ is methyl, $R^3$ is carboxy, A is a group of the formula:

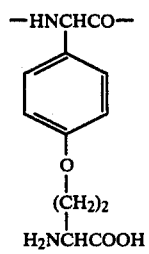

R⁵ is hydrogen and R⁶ is α-carboxy-4-hydroxybenzyl.
27. A compound according to claim 1, wherein
R¹ is propionyl, n is an integer of 1,
R² is methyl, R³ is carboxy, A is a group of the formula:

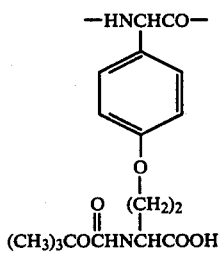

R⁵ is hydrogen and R⁶ is α-carboxy-4-hydroxybenzyl.
28. A compound according to claim 1, wherein
R¹ is propionyl, n is an integer of 1,
R² is methyl, R³ is carboxy, A is a group of the formula:

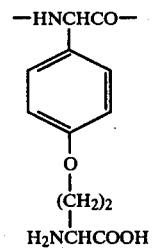

R⁵ is hydrogen and R⁶ is α-carboxy-4-hydroxybenzyl.
29. A compound according to claim 1, wherein
R¹ is octanoyl, n is an integer of 1,
R² is methyl, R³ is benzyloxycarbonyl,
A is a group of the formula:

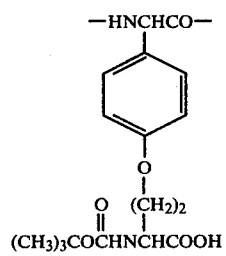

R⁵ is hydrogen and R⁶ is α-carboxy-4-hydroxybenzyl.
30. A compound according to claim 1, wherein
R¹ is octanoyl, n is an integer of 1,
R² is methyl, R³ is carboxy, A is a group of the formula:

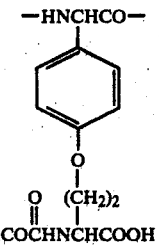

R⁵ is hydrogen and R⁶ is α-carboxy-4-hydroxybenzyl.
31. A compound according to claim 1, wherein
R¹ is octanoyl, n is an integer of 1,
R² is methyl, R³ is carboxy, A is a group of the formula:

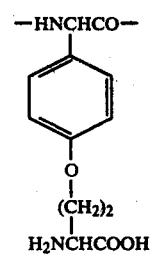

R⁵ is hydrogen and R⁶ is α-carboxy-4-hydroxybenzyl.
32. A compound according to claim 1, wherein
R¹ is stearoyl, n is an integer of 0,
R³ is benzyloxycarbonyl, A is a group of the formula:

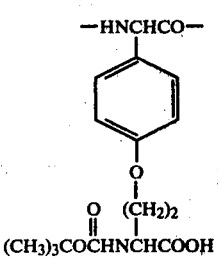

R⁵ is hydrogen and R⁶ is α-carboxy-4-hydroxybenzyl.
33. A compound according to claim 1, wherein
R¹ is stearoyl, n is an integer of 0,
R³ is carboxy, A is a group of the formula:

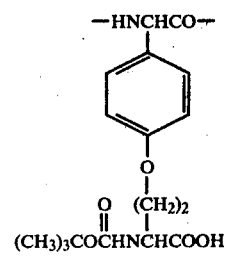

R⁵ is hydrogen and R⁶ is α-carboxy-4-hydroxybenzyl.
34. A compound according to claim 1, wherein
R¹ is stearoyl, n is an integer of 0,
R³ is carboxy, A is a group of the formula:

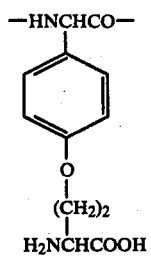

R[5] is hydrogen and R[6] is α-carboxy-4-hydroxybenzyl.
35. A compound according to claim 1, wherein R[1] is 2-acetoxypropionyl, n is an integer of 0, R[3] is benzyloxycarbonyl, A is a group of the formula:

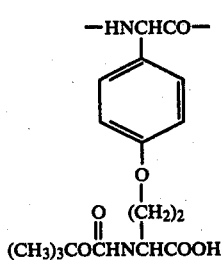

R[5] is hydrogen and R[6] is α-carboxy-4-hydroxybenzyl.
36. A compound according to claim 1, wherein R[1] is 2-acetoxypropionyl, n is an integer of 0, R[3] is carboxy, A is a group of the formula:

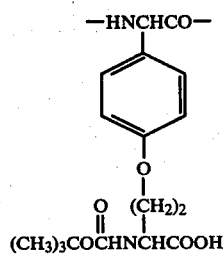

R[5] is hydrogen and R[6] is α-carboxy-4-hydroxybenzyl.
37. A compound according to claim 1, wherein R[1] is 2-hydroxypropionyl, n is an integer of 0, R[3] is carboxy, A is a group of the formula:

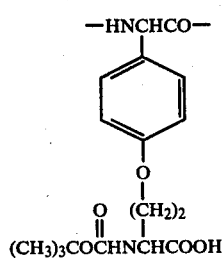

R[5] is hydrogen and R[6] is α-carboxy-4-hydroxybenzyl.
38. A compound according to claim 1, wherein R[1] is 2-hydroxypropionyl, n is an integer of 0, R[3] is carboxy, A is a group of the formula:

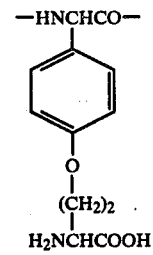

R[5] is hydrogen and R[6] is α-carboxy-4-hydroxybenzyl.
39. A compound according to claim 1, wherein R[1] is heptanoyl, n is an integer of 0, R[3] is benzyloxycarbonyl, A is a group of the formula:

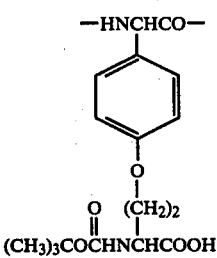

R[5] is hydrogen and R[6] is α-carboxy-4-hydroxybenzyl.
40. A compound according to claim 1, wherein R[1] is heptanoyl, n is an integer of 0, R[3] is carboxy, A is a group of the formula:

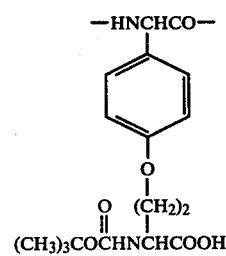

R[5] is hydrogen and R[6] is α-carboxy-4-hydroxybenzyl.
41. A compound according to claim 1, wherein R[1] is heptanoyl, n is an integer of 0, R[3] is carboxy, A is a group of the formula:

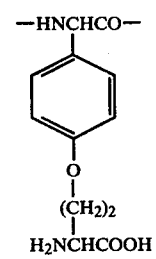

R[5] is hydrogen and R[6] is α-carboxy-4-hydroxybenzyl.
42. A compound according to claim 1, wherein R[1] is acetyl, n is an integer of 0, R[3] is benzyloxycarbonyl, A is a group of the formula:

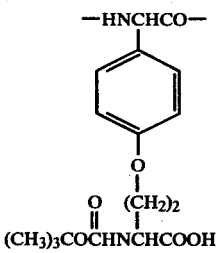

$R^5$ is hydrogen and $R^6$ is α-carboxy-4-hydroxybenzyl.
43. A compound according to claim 1, wherein
$R^1$ is acetyl, n is an integer of 0,
$R^3$ is carboxy, A is a group of the formula:

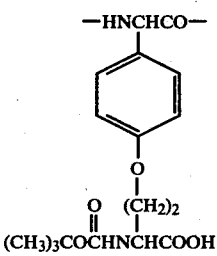

$R^5$ is hydrogen and $R^6$ is α-carboxy-4-hydroxybenzyl.
44. A compound according to claim 1, wherein
$R^1$ is acetyl, n is an integer of 0,
$R^3$ is carboxy, A is a group of the formula:

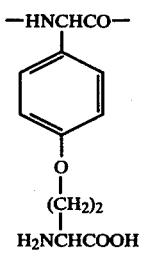

$R^5$ is hydrogen and $R^6$ is α-carboxy-4-hydroxybenzyl.
45. A compound according to claim 1, wherein
$R^1$ is behenoyl, n is an integer of 1, $R^2$ is methyl,
$R^3$ is carboxy, A is a group of the formula:

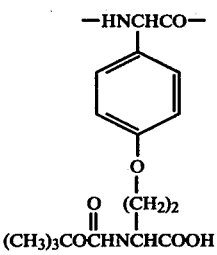

$R^5$ is hydrogen and $R^6$ is α-carboxy-4-hydroxybenzyl.
46. A compound according to claim 1, wherein
$R^1$ is behenoyl, n is an integer of 1, $R^2$ is methyl,
$R^3$ is carboxy, A is a group of the formula:

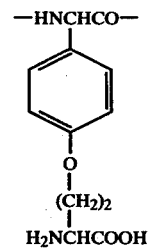

$R^5$ is hydrogen and $R^6$ is α-carboxy-4-hydroxybenzyl.
47. A compound according to claim 1, wherein
$R^1$ is 2-acetoxypropionyl, n is an integer of 1,
$R^2$ is methyl, $R^3$ is benzyloxycarbonyl, A is a bond,
$R^5$ is hydrogen and $R^6$ is α-carboxy-4-hydroxybenzyl.
48. A compound according to claim 1, wherein
$R^1$ is 2-hydroxypropionyl, n is an integer of 1,
$R^2$ is methyl, $R^3$ is carboxy, A is a bond, $R^5$ is hydrogen and $R^6$ is α-carboxy-4-hydroxybenzyl.
49. A compound according to claim 1, wherein
$R^1$ is octanoyl, n is an integer of 1, $R^2$ is methyl,
$R^3$ is benzyloxycarbonyl, A is a bond, $R^5$ is hydrogen and $R^6$ is α-carboxy-4-hydroxybenzyl.
50. A compound according to claim 1, wherein
$R^1$ is octanoyl, n is an integer of 1, $R^2$ is methyl,
$R^3$ is carboxy, A is a bond, $R^5$ is hydrogen and $R^6$ is α-carboxy-4-hydroxybenzyl.
51. A compound according to claim 1, wherein
$R^1$ is stearoyl, n is an integer of 1, $R^2$ is methyl,
$R^3$ is benzyloxycarbonyl, A is a bond, $R^5$ is hydrogen and $R^6$ is α-carboxy-4-hydroxybenzyl.
52. A compound according to claim 1, wherein
$R^1$ is stearoyl, n is an integer of 1, $R^2$ is methyl,
$R^3$ is carboxy, A is a bond, $R^5$ is hydrogen and $R^6$ is α-carboxy-4-hydroxybenzyl.
53. A compound according to claim 1, wherein
$R^1$ is 2-acetoxypropionyl, n is an integer of 1,
$R^2$ is methyl, $R^3$ is benzyloxycarbonyl, A is a group of the formula:

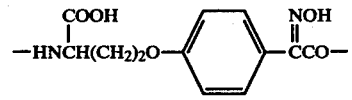

$R^5$ is hydrogen and $R^6$ is α-carboxy-4-hydroxybenzyl.
54. A compound according to claim 1, wherein
$R^1$ is 2-hydroxypropionyl, n is an integer of 1,
$R^2$ is methyl, $R^3$ is carboxy, A is a group of the formula:

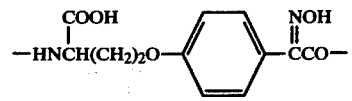

$R^5$ is hydrogen and $R^6$ is α-carboxy-4-hydroxybenzyl.
55. A compound according to claim 1, wherein
$R^1$ is 2-acetoxypropionyl, n is an integer of 1,
$R^2$ is methyl, $R^3$ is carboxy, A is a group of the formula:

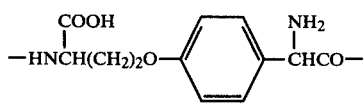

$R^5$ is hydrogen and $R^6$ is α-carboxy-4-hydroxypropionyl.

56. A compound according to claim 1, wherein $R^1$ is 2-hydroxypropionyl, n is an integer of 1, $R^2$ is methyl, $R^3$ is carboxy, A is a group of the formula:

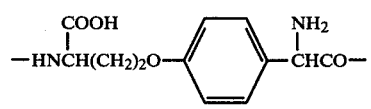

$R^5$ is hydrogen and $R^6$ is α-carboxy-4-hydroxybenzyl.

57. A compound according to claim 1, wherein $R^1$ is heptanoyl, n is an integer of 0, $R^3$ is benzyloxycarbonyl, A is a group of the formula:

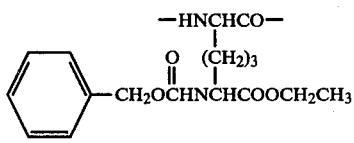

$R^5$ is ethoxycarbonyl and $R^6$ is 2,4-dimethoxybenzyl.

58. A compound according to claim 1, wherein $R^1$ is heptanoyl, n is an integer of 0, $R^3$ is carboxy, A is a group of the formula:

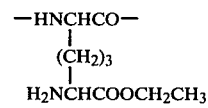

$R^5$ is ethoxycarbonyl and $R^6$ is 2,4-dimethoxybenzyl.

59. A compound according to claim 1, wherein $R^1$ is heptanoyl, n is an integer of 0, $R^3$ is benzyloxycarbonyl, A is a group of the formula:

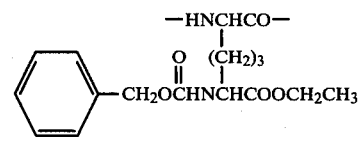

$R^5$ is ethoxycarbonyl and $R^6$ is hydrogen.

60. A compound according to claim 1, wherein $R^1$ is heptanoyl, n is an integer of 0, $R^3$ is carboxy, A is a group of the formula:

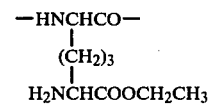

$R^5$ is ethoxycarbonyl and $R^6$ is hydrogen.

61. A compound according to claim 1, wherein $R^1$ is heptanoyl, n is an integer of 0, $R^3$ is carboxy, A is a group of the formula:

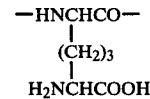

$R^5$ is carboxy and $R^6$ is hydrogen.

* * * * *